(12) United States Patent
Koyama et al.

(10) Patent No.: US 6,921,656 B1
(45) Date of Patent: Jul. 26, 2005

(54) POLYPEPTIDES HAVING GLUCOAMYLASE ACTIVITY

(75) Inventors: Nobuto Koyama, Kyoto (JP); Toshitake Okui, Shiga (JP); Hikaru Takakura, Shiga (JP); Kiyozo Asada, Shiga (JP); Ikunoshin Kato, Kyoto (JP)

(73) Assignee: Takara Bio Inc., Shiga (JP)

( * ) Notice: Subject to any disclaimer, the term of this patent is extended or adjusted under 35 U.S.C. 154(b) by 257 days.

(21) Appl. No.: 10/048,621

(22) PCT Filed: Jul. 26, 2000

(86) PCT No.: PCT/JP00/04956

§ 371 (c)(1),
(2), (4) Date: Feb. 4, 2002

(87) PCT Pub. No.: WO01/09348

PCT Pub. Date: Feb. 8, 2001

(30) Foreign Application Priority Data

Aug. 2, 1999 (JP) .......................................... 11-218778

(51) Int. Cl.$^7$ ............................. C12N 9/34; C12N 1/21; C12N 15/52; C07H 21/04
(52) U.S. Cl. ............... 435/205; 435/252.3; 435/252.33; 435/320.1; 536/23.2
(58) Field of Search ................................. 435/201, 202, 435/252.3, 252.33, 320.1, 205; 536/23.2

(56) References Cited

FOREIGN PATENT DOCUMENTS

| EP | 0 648 843 | 4/1995 |
|---|---|---|
| WO | WO 90/11352 | 10/1990 |

OTHER PUBLICATIONS

Maeder et al. (Aug. 1999) Genetics, vol. 152(4), pp. 1299–1305.*
Weiss (Feb. 25, 2002) GenBank accession AE010170.*
Laderman et al., "α–Amylase from the Hyperthermophilic Archaebacterium *Pyrococcus furiosus*", *The Journal of Biological Chemistry*, (1993), vol. 268, No. 32, pp. 24402–24407.
Lawson et al., "Nucleotide Sequence and X–ray Structure of Cyclodextrin Glycosyltransferase from *Bacillus circulans* Strains 251 in a Maltose–dependent Crystal Form", *Journal of Molecular Biology*, (1994), vol. 236, pp. 590–600.

Jørgensen et al., Cloning, Sequencing, Characterization, and Expression of an Extracellular α–Amylase from the Hyperthermophilic Archaeon *Pyrococcus furiosus*, in *Escherichia coli* and *Bacillus subtilis, Journal of Biological Chemistry*, (1997), vol. 272, No. 26, pp. 16335–16342.

Costantino et al., "Purification and Characterization of an α–Glucosidase from a Hypertermophilic Archaebacterium, *Pyrococcus furiosus*, Exhibiting a Temperature Optimum of 105 to 115°C", *Journal of Bacteriology*, (1990), vol. 172, No. 7, pp. 3654–3660.

Bauer et al., "An Endoglucanase, Eg1A, from the Hyperthermophilic Archaeon *Pyrococcus furiosus*, Hydrolyzes β–1,4 Bonds in Mixed–Linkage (1→3), (1→4)–β–D–Glucans and Cellulose", *Journal of Bacteriology*, (1999), vol. 181, No. 1, pp. 284–290.

Voorhorst et al., Characterization of the celB Gene Coding for β–Glucosidase from the Hyperthermophilic Archaeon *Pyrococcus furiosus* and Its Expression and Site–Directed Mutation in *Escherichia coli, Journal of Bacteriology*, vol. 177, No. 24, pp. 7105–7111.

B. Costanzo et al; "Starch–hydrolyzing enzymes from thermophilic archaea and bacteria", *Current Opinion in Chemical Biology*, vol. 6, No. 2, pp. 151–160, Apr. 2002.

Dong et al; "Cloning, sequencing, and expression of the gene encoding extracellular alpha–amylase from *Pyrococcus furiosus* and biochemical characterization of the recombinant enzyme"; *Applied and Environmental Microbiology*, vol. 63, No. 9, pp. 3569–3576; Sep. 1997.

K. Laderman et al; "The purification and Characterization of an Extremely Thermostable alpha–amylase from the hyperthermophilic archaebacterium *Pyrococcus furiosus*"; *Journal of Biological Chemistry, American Society of Biological Chemists*; vol. 268, No. 32, pp. 24394–24401, Nov. 1993.

* cited by examiner

*Primary Examiner*—Elizabeth Slobodyansky
(74) *Attorney, Agent, or Firm*—Browdy and Neimark, P.L.L.C.

(57) ABSTRACT

Polypeptides having the amino acid sequence represented by SEQ ID NO:6 in Sequence Listing or an amino acid sequence derived from the above sequence by at least one of deletion, addition, insertion or substitution of one or more amino acids and showing a thermophilic glucoamylase activity.

4 Claims, 7 Drawing Sheets

POLYPEPTIDES HAVING GLUCOAMYLASE ACTIVITY

TECHNICAL FIELD

The present invention relates to a polypeptide, more specifically, a polypeptide having a glucoamylase activity, which is useful for profitable utilization of biomass. The present invention also relates to a gene that is useful for producing said polypeptide by genetic engineering.

BACKGROUND ART

Two enzymes each having an activity of releasing D-glucose linked at a non-reducing end through an α-1,4 bond, glucan 1,4-α-glucosidase and α-glucosidase, are known.

Glucan 1,4-α-glucosidase (EC 3.2.1.3) is also called 1,4-α-D-glucan glucohydrolase or glucoamylase. It is an enzyme that acts on a non-reducing end of a polymer of D-glucopyranose linked through α-1,4 bonds to release β-D-glucose. Glucan 1,4-α-glucosidases derived from the following are currently known: fungi such as those of genus *Aspergillus*, genus *Mucor*, genus *Rhizopus*, genus *Piricularia*, genus *Thermomyces* and genus *Trichoderma*; yeasts such as those of genus *Endomyces* and genus *Saccharomyces*; and a bacterium of genus *Clostridium*. This enzyme, like α-amylase, is an important enzyme used in a process of hydrolyzing starch. Thus, the enzyme is industrially utilized in wide variety of fields including production of glucose, isomerized sugars and oligosaccharides, as well as production of liquors and fermented alcohol.

Glucose is usually produced from starch as follows. Starch is gelatinized by cooking. The gelatinized starch is liquefied by allowing α-amylase to act on it at about 80 C. Then, saccharification is carried out by allowing glucan 1,4-α-glucosidase to act at 55 to 60 C. The liquefaction is carried out at a high temperature because the gelatinized starch is highly viscous and because thermostable α-amylases have been put to practical use. It is desirable to select a temperature of 55 C. or above for the saccharification in order to avoid contamination with microorganisms. However, if a commonly used enzyme derived from a fungus is used, one must select a temperature of 60 C. or below because of the thermostability of the enzyme. Accordingly, it is impossible to carry out the steps of liquefaction and saccharification at the same time because their optimal temperatures are different from each other, resulting in a great wasteful cost for energy.

α-Glucosidase (EC 3.2.1.20) is an enzyme that acts on an α-glucoside bond at a non-reducing end to release α-D-glucose. It is widely present in animals, plants and microorganisms. α-Glucosidases are classified into groups (1) to (3) based on the substrate specificity as follows: (1) ones that act on a wide variety of hetero and homo α-glucoside compounds; (2) ones that are highly specific for α-1,4-glucooligosaccharides and that have relatively weak activities on high molecular weight glucan and heteroglucoside; and (3) ones that are highly specific for α-1,4-glucoside bonds or that also act on starch or glycogen. Among these, those belonging to the group (3) are often called glucoamylases ("Oyo Kosogaku", Tsujisaka et al. (eds), Kodansha (1979) pp. 56).

Hyperthermophilic microorganisms, which are adapted to high temperature environment, produce highly thermostable enzymes. *Pyrococcus furiosus*, a hyperthermophilic archaebacterium, is known to produce saccharide-hydrolyzing enzymes such as α-amylase, α-glucosidase, β-glycosidase and β-glucanase. Genes for some of these enzymes have been cloned (The Journal of Biological Chemistry, 268:24402–24407 (1993); The Journal of Biological Chemistry, 272:16335–16342 (1997); Journal of Bacteriology, 172:3654–3660 (1990); Journal of Bacteriology, 177:7105–7111 (1995); Journal of Bacteriology, 181:284–290 (1999)). However, there is no known hyperthermophilic microorganism producing glucan 1,4-α-glucosidase or hyperthermostable glucan 1,4-α-glucosidase. Furthermore, known α-glucosidases produced by hyperthermophilic microorganisms including *Pyrococcus furiosus* act only on low molecular weight substrates and do not digest high molecular weight substrates such as starch.

OBJECTS OF INVENTION

The main object of the present invention is to provide an industrially advantageous polypeptide having a thermostable glucoamylase activity, a gene encoding said polypeptide and a method of producing said polypeptide by genetic engineering.

SUMMARY OF INVENTION

The present invention is outlined as follows. The first aspect of the present invention relates to a polypeptide having the amino acid sequence of SEQ ID NO:6 or an amino acid sequence in which one or more amino acid residue is deleted, added, inserted and/or substituted in the amino acid sequence of SEQ ID NO:6 and having a thermostable glucoamylase activity. The second aspect of the present invention relates to a nucleic acid encoding the polypeptide of the first aspect. The third aspect of the present invention relates to a nucleic acid encoding a polypeptide having a thermostable glucoamylase activity which is capable of hybridizing to the nucleic acid of the second aspect under stringent conditions. The fourth aspect of the present invention relates to a recombinant DNA containing the nucleic acid of the second or third aspect. The fifth aspect of the present invention relates to a transformant transformed with the recombinant DNA of the fourth aspect. The sixth aspect of the present invention relates to a method for producing the polypeptide of the first aspect, the method comprising culturing the transformant of the fifth aspect and collecting a polypeptide having a thermostable glucoamylase activity from the culture. The seventh aspect of the present invention relates to a method for producing glucose, the method comprising allowing the polypeptide of the first aspect to act on a polymer of D-glucopyranose liked through α-1,4 bonds to release glucose. The eighth aspect of the present invention relates to a method for producing an oligosaccharide, the method comprising allowing the polypeptide of the first aspect to act on a polymer of D-glucopyranose liked through α-1,4 bonds to generate an oligosaccharide. The ninth aspect of the present invention relates to a method for producing a cyclodextrin, the method comprising allowing the polypeptide of the first aspect to act on a polymer of D-glucopyranose liked through α-1,4 bonds to generate a cyclodextrin.

As a result of intensive studies, the present inventors have found that a gene encoding a novel polypeptide exists on the *Pyrococcus furiosus* genome. Furthermore, the present inventors have surprisingly found that the polypeptide has a thermostable glucoamylase activity although the amino acid sequence of the polypeptide is highly homologous only to those of various α-amylases and cyclomaltodextrin glucanotransferases derived from bacteria. The present inventors have further investigated to establish a method for producing the polypeptide by genetic engineering. Thus, the present invention has been completed.

DETAILED DESCRIPTION OF THE INVENTION

Figure 1:
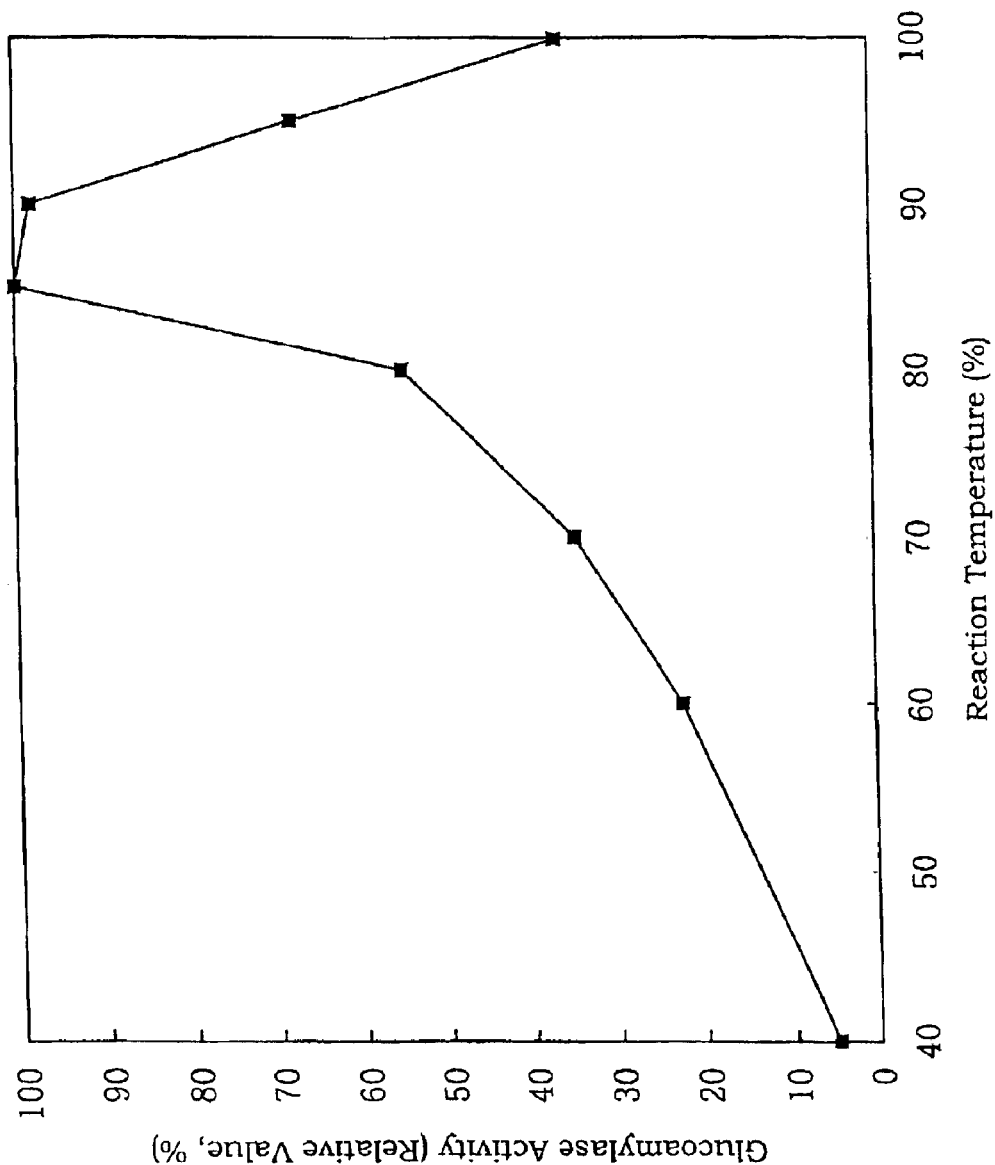
FIG. 1 illustrates the relationship between the reaction temperature and the glucoamylase activity of the polypeptide of the present invention.

1. The Polypeptide of the Present Invention

The polypeptide of the present invention has the amino acid sequence of SEQ ID NO:6 or an amino acid sequence in which one or more amino acid residue is deleted, added, inserted and/or substituted in the amino acid sequence of SEQ ID NO:6, and has a thermostable glucoamylase activity.

As used herein, a glucoamylase activity means an activity that sequentially hydrolyzes glucoside bonds in a polysaccharide or an oligosaccharide consisting of D-glucopyranose linked through $\alpha$-1,4 bonds from the non-reducing end to release D-glucose. An enzyme that releases $\beta$-D-glucose is called glucan 1,4-$\alpha$-glucosidase (EC 3.2.1.3). An enzyme that releases $\alpha$-D-glucose is called $\alpha$-glucosidase (EC 3.2.1.20). As used herein, having a glucoamylase activity means that at least one of the two catalytic activities is exhibited.

Methods for determining a glucoamylase activity are exemplified by known methods. Such methods include a method in which an enzymatic reaction is carried out using amylose as a substrate, and the increase in the amount of reducing sugar is determined according to the Park & Johnson method, and a method in which D-glucose released upon the same enzymatic reaction is measured according to an enzymatic method using glucose oxidase.

The polypeptide of the present invention has a glucoamylase activity. The polypeptides of the present invention also include polypeptides that have, in addition to the glucoamylase activity, other activities such as a hydrolase activity (e.g., an $\alpha$-amylase activity or a $\beta$-amylase activity) or a glycosyltransferase activity (e.g., a cyclomaltodextrin glucanotransferase). For example, the polypeptide of the present invention having an amino acid sequence of SEQ ID NO:6 has a glycosyltransferase activity because when an oligosaccharide such as maltose, maltotriose or maltotetraose is used as a substrate, it generates glucose and a product having a higher molecular weight than that of an oligosaccharide as a substrate.

The polypeptide of the present invention has a thermostable glucoamylase activity. Although it is not intended to limit the present invention, "having a thermostable glucoamylase activity" means that the polypeptide exhibits a glucoamylase activity at a temperature of 70° C. or above, preferably 80° C. or above, more preferably 85° C. or above, most preferably 90° C. or above.

The polypeptides of the present invention include a polypeptide having an amino acid sequence in which one or more amino acid residue is deleted, added, inserted and/or substituted in the amino acid sequence of SEQ ID NO:6 as long as it has a thermostable glucoamylase activity.

A mutation such as deletion, insertion, addition or substitution of an amino acid in an amino acid sequence may be generated in a naturally occurring polypeptide. Such mutation may be generated due to a polymorphism or a mutation of the DNA encoding the polypeptide, or due to a modification of the polypeptide in vivo or during purification after synthesis. However, it is known that such a mutated polypeptide may exhibit physiological or biological activities substantially equivalent to those of a polypeptide without a mutation if such a mutation is present in a portion that is not important for the retention of the activity or the structure of the polypeptide.

This is applicable to a polypeptide in which such a mutation is artificially introduced into an amino acid sequence of a polypeptide. In this case, it is possible to generate more various mutations. For example, it is known that a polypeptide in which a cysteine residue in the amino acid sequence of human interleukin-2 (IL-2) is replaced by a serine retains the interleukin-2 activity (Science, 224:1431 (1984)).

Furthermore, it is known that certain polypeptides have peptide regions that are not indispensable to their activities. Such peptide regions are exemplified by a signal peptide in a polypeptide to be secreted extracellularly or a prosequence found in a precursor of a protease. Most of such regions are removed after translation or upon conversion into an active polypeptide. Such a polypeptide has a primary structure different from that of a polypeptide without the region to be removed, but finally exhibits an equivalent function. A gene having a nucleotide sequence of SEQ ID NO:2 which is isolated according to the present invention encodes a polypeptide having the amino acid sequence of SEQ ID NO:1. This polypeptide has a thermostable glucoamylase activity. A signal peptide-like sequence consisting of 19 amino acid residues is present at the amino terminus of the encoded polypeptide. A polypeptide in which the signal peptide has been removed from the polypeptide, i.e., the polypeptide having the amino acid sequence of SEQ ID NO:6, also has a thermostable clucoamylase activity. Thus, the polypeptides of the present invention include both of the above-mentioned two polypeptides.

When a polypeptide is produced by genetic engineering, a peptide chain that is irrelevant to the activity of the polypeptide of interest may be added at the amino terminus or the carboxyl terminus of the polypeptide. For example, a fusion polypeptide, in which a portion of an amino terminus region of a polypeptide that is expressed at a high level in the host to be used is added at the amino terminus of the polypeptide of interest, may be expressed in order to increase the expression level of the polypeptide of interest. In another case, a peptide having an affinity with a specific substance may be added at the amino terminus or the carboxyl terminus of the polypeptide of interest in order to facilitate the purification of the expressed polypeptide. The added peptide may remain added if it does not have a harmful influence on the activity of the polypeptide of interest. If necessary, it may be engineered such that it can be removed from the polypeptide of interest by appropriate treatment, for example, by limited digestion with a protease.

Thus, a polypeptide having an amino acid sequence in which one or more amino acid residue is deleted, inserted, added and/or substituted in the amino acid sequence disclosed herein (SEQ ID NO:1) is encompassed by the present invention if it has a thermostable glucoamylase activity.

The polypeptides of the present invention include the mutant polypeptides as described in Examples below such as F206S, P142I, L337V, FS/PI and FS/LV.

The polypeptide of the present invention can be produced, for example, by (1) purification from a culture of a microorganism producing the polypeptide of the present invention, or (2) purification from a culture of a transformant containing a nucleic acid encoding the polypeptide of the present invention.

(1) Purification from culture a of a microorganism producing the polypeptide of the present invention The microorganism producing the polypeptide of the present invention is exemplified by *Pyrococcus furiosus* DSM3638 which can be purchased from Deutsche Sammlung von Mikroorganismen und Zellkulturen GmbH. The microorganism is cultured under conditions suitable for the growth of the microorganism. Preferably, culture conditions that increase the expression level of the polypeptide of interest are used. The polypeptide of interest produced in the cells or the culture medium can be purified according to a method conventionally used for purifying a protein.

A method conventionally used for culturing a hyperthermophile can be utilized for the cultivation of the above-mentioned strain. Nutrients that can be utilized by the strain are added to the culture medium. For example, starch can be used as a carbon source, and Tryptone, peptone and yeast extract can be used as nitrogen sources. A metal salt such as a magnesium salt, a sodium salt or an iron salt may be added to a culture medium as a trace element. In addition, it may be advantageous to use artificial seawater for the preparation of a culture medium, for example. A clear culture medium that does not contain solid sulfur is desirable. By using such a culture medium, the growth of cells can be readily monitored by measuring the turbidity of the culture.

The culture may be a standing culture or a spinner culture. For example, a dialysis culture method as described in Applied and Environmental Microbiology, 55:2086–2088 (1992) may be used. In general, the culture temperature is preferably about 95° C. Usually, a considerable amount of a polypeptide is accumulated in the culture after culturing for about 16 hours. It is preferable to determine the culture conditions depending on the strain or the composition of the culture medium to be used such that the productivity of the polypeptide becomes maximal.

A cell-free extract is first prepared in order to obtain a polypeptide. The cell-free extract can be prepared, for example, by collecting cells from a culture by centrifugation, filtration or the like and then disrupting the cells. A cell disruption method highly effective for extracting the enzyme of interest may be selected from sonication, disruption using beads, treatment with a lytic enzyme and the like. If the polypeptide is secreted into a culture supernatant, the polypeptide in the culture supernatant is concentrated by ammonium sulfate precipitation, ultrafiltration or the like. The concentrated polypeptide is used as a cell-free extract. A method conventionally used for purifying a protein can be used to isolate the polypeptide from the thus obtained cell-free extract. For example, ammonium sulfate precipitation, ion exchange chromatography, hydrophobic chromatography, gel filtration chromatography and the like can be used in combination.

(2) Purification from Culture of Transformant Transformed with Recombinant DNA Containing Nucleic Acid Encoding the Polypeptide of the Present Invention The polypeptide of the present invention can be obtained from a transformant transformed with a recombinant DNA that contains a nucleic acid encoding the polypeptide of the present invention, for example, a nucleic acid having a nucleotide sequence of SEQ ID NO:2 or 7. A polypeptide having an amino acid sequence of SEQ ID NO:1 is produced using a nucleic acid having a nucleotide sequence of SEQ ID NO:2. A polypeptide having an amino acid sequence of SEQ ID NO:6 is produced using a nucleic acid having a nucleotide sequence of SEQ ID NO:7.

The host to be transformed is not limited to specific one and exemplified by those conventionally used in a field of recombinant DNA including *Escherichia coli, Bacillus subtilis*, yeast, filamentous fungi, plants, animals, plant cultured cells and animal cultured cells.

For example, the polypeptide of the present invention can be obtained using *Escherichia coli* JM109 harboring pSJ3231, a plasmid in which a DNA having a nucleotide sequence of SEQ ID NO:2 is linked downstream from a lac promoter. *Escherichia coli* JM109 transformed with pSJ3231 is designated and indicated as *Escherichia coli* JM109/pSJ3231, and deposited on Jul. 30, 1999 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-7196.

The polypeptide can be expressed in cultured cells by culturing *Escherichia coli* JM109 harboring pSJ3231 under conventional culture conditions, for example, in LB medium (10 g/l Tryptone, 5 g/l yeast extract, 5 g/l NaCl, pH 7.2) containing 100 µg/ml of ampicillin at 37° C. until logarithmic growth phase, adding isopropyl-β-D-thiogalactopyranoside at a final concentration of 0.2 mM thereto and further culturing at 37° C.

Cells are collected by centrifugation after cultivation, disrupted by sonication, and a supernatant collected by centrifugation is used as a cell-free extract. This cell-free extract exhibits a thermostable glucoamylase activity. The polypeptide of the present invention can be purified from the cell-free extract by using known methods such as ion exchange chromatography, gel filtration, hydrophobic chromatography and ammonium sulfate precipitation. Naturally, a partially purified product obtained during the purification process as described above also exhibits a glucoamylase activity. Since the polypeptide of the present invention expressed in *Escherichia coli* JM109 harboring pSJ3231 is highly thermostable, the cultured cells and/or the cell-free extract may be heated, for example, at 80° C. for 10 minutes to remove heat-denatured insoluble proteins derived from the host in order to purify the polypeptide.

Alternatively, the polypeptide of the present invention having the amino acid sequence of SEQ ID NO:6 can be obtained in a similar manner using *Escherichia coli* harboring pET21amyCΔS as described in Examples below.

As described above, when the polypeptide of the present invention is expressed at normal temperature (e.g., 37° C.) using a transformant harboring a nucleic acid encoding the polypeptide, the resulting expression product retains the activity, the thermostability and the like. That is, the polypeptide of the present invention can assume its inherent higher-order structure even if it is expressed at a temperature quite different from the growth temperature of the original producer cell.

Some of the enzymological properties of the polypeptide of the present invention obtained as described above (e.g., the polypeptide having an amino acid sequence of SEQ ID NO:6) are shown below.

(1) Action:

The polypeptide of the present invention hydrolyzes amylose to generate glucose and oligosaccharides.

In addition, the polypeptide of the present invention acts on amylose to generate a cyclodextrin.

(2) Optimal Temperature: it Exhibits Maximum Activity at 85–90 C.

(3) Optimal pH: it Exhibits Maximum Activity at pH 5–6.

(4) The Stability is Increased in the Presence of $CaCl_2$.

(5) The Activity is Inhibited by EDTA.

2. The Nucleic Acid of the Present Invention

The nucleic acid of the present invention is a nucleic acid that encodes the polypeptide of the present invention as described above. Specifically, it is exemplified by (1) a nucleic acid encoding a polypeptide having the amino acid sequence of SEQ ID NO:6 or an amino acid sequence in which one or more amino acid residue is deleted, added, inserted and/or substituted in the amino acid sequence of SEQ ID NO:6 and having a thermostable glucoamylase activity; (2) a nucleic acid having the nucleotide sequence of SEQ ID NO:7; and (3) a nucleic acid encoding a polypeptide having a thermostable glucoamylase activity which is capable of hybridizing to the nucleic acid of (1) or (2) above under stringent conditions.

As used herein, a nucleic acid means a single-stranded or double-stranded DNA or RNA. If the nucleic acid of (2) above is an RNA, it is represented by a nucleotide sequence in which T is replaced by U in the nucleotide sequence of SEQ ID NO:7, for example.

For example, the nucleic acid of the present invention can be obtained as follows.

The nucleic acid of (2) above having the nucleotide sequence of SEQ ID NO:7 can be isolated as follows. A genomic DNA is obtained according to a conventional method from *Pyrococcus furiosus* DSM3638 cultured as described above for the polypeptide of the present invention. The genomic DNA is used to construct a DNA library. The nucleic acid can be isolated from the DNA library. Also, the nucleic acid can be obtained by amplifying a nucleic acid having a nucleotide sequence of SEQ ID NO:7 by a polymerase chain reaction (PCR) using the genomic DNA as a template.

Furthermore, a nucleic acid encoding a polypeptide having a thermostable glucoamylase activity similar to that of the polypeptide of the present invention can be obtained on the basis of the nucleotide sequence of the nucleic acid encoding the polypeptide of the present invention provided by the present invention (e.g., the nucleotide sequence of SEQ ID NO:7). Specifically, a DNA encoding a polypeptide having a thermostable glucoamylase activity can be screened by using the nucleic acid encoding the polypeptide of the present invention or a portion of the nucleotide sequence as a probe for hybridization from a DNA extracted from cells or PCR products obtained using the DNA as a template. Alternatively, a DNA encoding a polypeptide having a thermostable glucoamylase activity can be amplified using a gene amplification method such as a PCR using a primer designed based on the above-mentioned nucleotide sequence. Additionally, a DNA encoding a polypeptide having a thermostable glucoamylase activity can be chemically synthesized. The nucleic acids of (1) or (3) above can be obtained according to such a method.

A nucleic acid fragment containing only a portion of the nucleic acid of interest may be obtained according to the above-mentioned method. In this case, the entire nucleic acid of interest can be obtained as follows. The nucleotide sequence of the obtained nucleic acid fragment is determined to confirm that the fragment is a portion of the nucleic acid of interest. Hybridization is carried out using the nucleic acid fragment or a portion thereof as a probe. Alternatively, a PCR is carried out using a primer synthesized on the basis of the nucleotide sequence of the nucleic acid fragment.

"Hybridize under stringent conditions" refers to being capable of hybridizing under conditions as described in T. Maniatis et al. (eds.), Molecular Cloning: A Laboratory Manual 2nd ed., Cold Spring Harbor Laboratory (1989), for example, under the following conditions. A membrane onto which a nucleic acid is immobilized is incubated with a probe in 6×SSC (1×SSC: 0.15 M NaCl, 0.015 M sodium citrate, pH 7.0) containing 0.5% SDS, 0.1% bovine serum albumin (BSA), 0.1% polyvinylpyrrolidone, 0.1% Ficoll 400 and 0.01% denatured salmon sperm nucleic acid at 50° C. for 12 to 20 hours. After incubation, the membrane is washed in 2×SSC containing 0.5% SDS at 37° C. while changing the SSC concentration down to 0.1× and the temperature up to 50° C. until the signal from the immobilized nucleic acid can be distinguished from background, and the probe is then detected. The activity of the protein encoded by the thus obtained novel nucleic acid is determined as described above, thereby confirming whether or not the nucleic acid is the nucleic acid of interest.

If an oligonucleotide probe is used, "stringent conditions" refer to, for example, incubation at a temperature of [Tm−25° C.] overnight in a solution containing 6×SSC, 0.5% SDS, 5×Denhardt's and 0.01% denatured salmon sperm nucleic acid although it is not intended to limit the present invention.

Tm of an oligonucleotide probe or primer can be determined, for example, according to the following equation:

$$Tm=81.5-16.6(\log_{10}[Na+])+0.41(\% \ G+C)-(600/N)$$

wherein N is the chain length of the oligonucleotide probe or primer; % G+C is the content of guanine and cytosine residues in the oligonucleotide probe or primer.

If the chain length of the oligonucleotide probe or primer is shorter than 18 bases, Tm can be estimated, for example, as the sum of the product of the number of A+T (adenine and thymine) residues multiplied by 2(° C.) and the product of the number of G+C residues multiplied by 4(° C.): [(A+T)×2+(G+C)×4].

According to the present invention, a nucleic acid which is capable of hybridizing to the nucleic acid encoding the polypeptide of the present invention under stringent conditions is encompassed by the present invention as long as it encodes a polypeptide having a thermostable glucoamylase activity even if it does not have the same nucleotide sequence as that disclosed herein, as described above.

It is known that one to six codon(s) (a combination of three bases), which defines an amino acid in a gene, is assigned for each amino acid. Thus, many nucleic acids can encode one specific amino acid sequence although it depends on the amino acid sequence. Nucleic acids are not necessarily stable in nature. Generation of a mutation in a nucleotide sequence is not unusual. A mutation generated in a nucleic acid may not alter the encoded amino acid sequence (called a silent mutation). In this case, it can be said that a different nucleic acid encoding the same amino acid sequence is generated. Thus, it cannot be denied that various nucleic acids encoding the same amino acid sequence can be generated in the course of passage of an organism containing a nucleic acid encoding one specific amino acid sequence. Furthermore, it is not difficult to artificially produce various nucleic acids encoding the same amino acid sequence if one uses various genetic engineering techniques.

For example, if a codon used in an original nucleic acid encoding a protein of interest is one whose codon usage is low in the host to be used for producing the protein by genetic engineering, the expression level of the protein may be low. In this case, the codon is artificially converted into one frequently used in the host without altering the encoded amino acid sequence aiming at elevating the expression level of the protein of interest (e.g., JP-B 7-102146). As described above, various nucleic acids encoding one specific amino acid sequence can be artificially prepared, of course. They may also be generated in nature.

The nucleic acid encoding the polypeptide of the present invention (e.g., a nucleic acid having the nucleotide sequence of SEQ ID NO:7) can be ligated to an appropriate vector to construct a recombinant DNA. The vector to be used for the construction of the recombinant DNA is not specifically limited. For example, plasmid vectors, phage vectors and virus vectors can be used. A suitable vector for the object of the recombinant DNA is selected.

Furthermore, a transformant can be produced by introducing the recombinant DNA into an appropriate host. The host to be used for the production of a transformant is not specifically limited. Microorganisms such as bacteria, yeasts and filamentous fungi as well as cultured cells from mammals, plants, insects and like can be used. The polypeptide of the present invention can be produced in large quantities by culturing the transformant to produce the polypeptide of the present invention in the culture.

3. The Method of Producing Glucose, Oligosaccharide or Cyclodextrin Using the Polypeptide of the Present Invention D-glucose can be released from a polymer of D-glucopyranose liked through α-1,4 bonds by using the polypeptide of the present invention. According to the present invention, the degree of polymerization of glucopyranose in the polymer of D-glucopyranose liked through α-1,4 bonds is not specifically limited. Maltose, amylose and starch are included. The polymers of D-glucopyranose liked through α-1,4 bonds according to the present invention also include a polymer that contains a bond other than the α-1,4 bond (e.g., an α-1,6 bond) or a saccharide other than D-glucose (e.g., fructose) in the molecule. The polypeptide of the present invention having the sequence of SEQ ID NO:1 is highly thermostable. Thus, it can efficiently digest a substrate partially due to synergistic effects with the change of the conformation and the physical properties of the substrate upon heating.

Specific reaction conditions are exemplified as follows. If a polypeptide having the amino acid sequence of SEQ ID NO:1 is used, D-glucose can be released by reacting it with substrate in 50 mM sodium acetate buffer (pH 5.5) at 80° C. Naturally, the optimal reaction conditions may vary depending on the type of the substrate (starch, maltose, etc.).

The polypeptide used for the method for producing glucose of the present invention is not limited to an isolated and purified polypeptide. A crude or partially purified polypeptide may be used as long as it does not have harmful influence on the production of glucose. The polypeptide of the present invention may be added to a substrate solution in a free form. However, the polypeptide is readily recovered after completion of the reaction if it is immobilized onto an appropriate carrier and reacted with a substrate.

Furthermore, it is possible to digest starch into D-glucose with high efficiency by using thermostable enzyme(s) such as α-amylase together with the polypeptide of the present invention.

Furthermore, the polypeptide of the present invention can be used to produce an oligosaccharide and a cyclodextrin.

An oligosaccharide or a cyclodextrin can be produced by reacting starch, amylose or an appropriate oligosaccharide as a substrate under conditions suitable for the polypeptide of the present invention as described above. Naturally, the reaction conditions may be appropriately adjusted depending on the type of the product of interest. Oligosaccharides obtained according to the method of the present invention are exemplified by maltooligosaccharides from maltose (G2) to maltooctaose (G8). Cyclodextrins obtained according to the method of the present invention are exemplified by α-cyclodextrin, β-cyclodextrin and γ-cyclodextrin.

EXAMPLES

The following examples further illustrate the present invention in detail but are not to be construed to limit the scope thereof.

Among the procedures described herein, basic procedures including preparation of plasmid DNAs and restriction enzyme digestion were carried out as described in Molecular Cloning: A Laboratory Manual 2nd ed. (supra). Unless otherwise stated, *Escherichia coli* JM109 was used as a host for the construction of plasmids using *Escherichia coli*. Transformed *E. coli* cells were cultured aerobically at 37° C. using LB medium (1% Tryptone, 0.5% yeast extract, 0.5% NaCl, pH 7.0) containing 100 µg/ml of ampicillin or LB plate prepared by adding agar at concentration of 1.5% to LB medium and solidifying the resulting mixture.

Example 1

Isolation of Gene Encoding Polypeptide Having Glucoamylase Activity (1) Preparation of Genomic DNA from *Pyrococcus furiosus*

*Pyrococcus furiosus* DSM3638 (purchased from Deutsche Sammlung von Mikroorganismen und Zellkulturen GmbH) was cultured as follows.

2 l of a medium containing 1% Tryptone (Difco Laboratories), 0.5% yeast extract (Difco Laboratories), 1% soluble starch (Nacalai Tesque), 3.5% Jamarine S Solid (Jamarine Laboratory), 0.5% Jamarine S Liquid (Jamarine Laboratory), 0.003% $MgSO_4$, 0.001% NaCl, 0.0001% $FeSO_4 \cdot 7H_2O$, 0.0001% $CoSO_4$, 0.0001% $CaCl_2 \cdot 7H_2O$, 0.0001% $ZnSO_4$, 0.1 ppm $CuSO_4 \cdot 5H_2O$, 0.1 ppm $KAl(SO_4)_2$, 0.1 ppm $H_3BO_3$, 0.1 ppm $Na_2MoO_4 \cdot 2H_2O$, 0.25 ppm $NiCl_2 \cdot 6H_2O$ was placed in a 2-l medium bottle, sterilized at 120° C. for 20 minutes, and bubbled with nitrogen gas to remove dissolved oxygen. Then, the above-mentioned strain was inoculated into the medium and cultured at 95° C. for 16 hours without shaking. After cultivation, cells were collected by centrifugation.

The resulting cells were then suspended in 4 ml of 50 mM Tris-HCl (pH 8.0) containing 25% sucrose. 2 ml of 0.2 M EDTA and 0.8 ml of lysozyme (5 mg/ml) were added to the suspension. The mixture was incubated at 20° C. for 1 hour. 24 ml of SET solution (150 mM NaCl, 1 mM EDTA, 20 mM Tris-HCl, pH 8.0), 4 ml of 5% SDS and 400 µl of proteinase K (10 mg/ml) were then added to the mixture. Incubation was further carried out at 37° C. for 1 hour. The reaction was terminated by extracting the mixture with phenol-chloroform. Then, ethanol precipitation was carried out to obtain a genomic DNA.

(2) Preparation of DNA Fragment Containing Gene Encoding Polypeptide Having Glucoamylase Activity An oligonucleotide aml-F1 having the nucleotide sequence of SEQ ID NO:3 and an oligonucleotide AMY-2N having the nucleotide sequence of SEQ ID NO:4 were synthesized on the basis of the nucleotide sequence of *Pyrococcus furiosus* genome. A PCR was carried out using these two oligonucleotides as primers and the above-mentioned genomic DNA as a template. The PCR was carried out according to the protocol attached to TaKaRa ExTaq (Takara Shuzo) as follows: 30 cycles of 94° C. for 0.5 minute, 55° C. for 1 minute and 72° C. for 5 minutes. The reaction mixture was subjected to agarose gel electrophoresis. An amplified DNA fragment of about 3.5-kb was extracted from the gel and purified. The nucleotide sequence of the about 3.5-kb amplified DNA fragment is shown as SEQ ID NO:5.

(3) Construction of Recombinant Plasmid pSJ3231

The about 3.5-kb amplified DNA fragment obtained in (2) above was digested with XbaI and SphI (both from Takara Shuzo), and subjected to agarose gel electrophoresis. A DNA fragment of about 2.3 kb containing the gene of interest was then extracted and purified. On the other hand, a plasmid vector pUC19 (Takara Shuzo) was digested with Xba I and SphI and dephosphorylated with alkaline phosphatase (Takara Shuzo). The two DNA fragments were ligated using DNA ligase (Takara Shuzo). The ligation mixture was used to transform *Escherichia coli* JM109 (Takara Shuzo). Several transformants were selected from the resulting transformants, and the size of each of DNA fragments inserted in plasmid DNAs harbored in the respective transformants was determined. A plasmid having the about 2.3-kb DNA fragment was purified. The nucleotide sequence of the thus obtained plasmid DNA was determined. Thus, a plasmid pSJ3231 having a DNA that is derived from the above-mentioned about 3.5-kb DNA fragment and has a nucleotide sequence of SEQ ID NO:2 was obtained. *Escherichia coli* JM109 harboring pSJ3231 was designated as *Escherichia coli* JM109/pSJ3231.

Example 2

Production of Polypeptide (1) Expression of Polypeptide

*Escherichia coli* JM109 harboring pSJ3231 prepared in Example 1 (3) or pUC19 as a vector control was separately inoculated into 5 ml of LB medium containing 100 µg/ml of ampicillin, and cultured aerobically at 37° C. overnight. The culture was inoculated into 20 ml of the same fresh medium at a concentration of 1%, and cultured aerobically at 37° C. When the turbidity reached $OD_{600}$=0.4 to 0.7, isopropyl-β-D-thiogalactopyranoside (IPTG, Takara Shuzo) was added at a final concentration of 0.2 mM. The cells were further cultured overnight. After cultivation, the cells were collected by centrifugation, suspended in 0.5 ml of 50 mM sodium acetate buffer (pH 5.5), disrupted by sonication and treated at 80° C. for 10 minutes. Supernatants obtained by centrifugation were concentrated by 20 times using Ultrafree-MC (Millipore) and used as cell-free extracts for determining activities as follows.

5 µl of the cell-free extract was mixed with an equal volume of 2× sample buffer (125 mM Tris-HCl (pH 6.8), 4% SDS, 20% glycerol, 0.005% Bromophenol Blue). The mixture was applied to SDS-polyacrylamide gel containing 0.1% soluble starch in the separation gel and electrophoresed according to a conventional method. After electrophoresis, the gel was washed three times each for 5 minutes in 50 mM sodium acetate buffer (pH 5.5) at room temperature and reacted in the same buffer at 80° C. for 1.5 hours. After reaction, the gel was briefly washed with water and stained with an iodine solution (an aqueous solution containing 10 mM $I_2$ and 1% KI)

As a result, digestion of starch was not observed for the cell-free extract prepared from *Escherichia coli* JM109 harboring pUC19. On the other hand, a clear band resulting from the digestion of starch was observed on the gel for the cell-free extract prepared from *Escherichia coli* JM109 harboring pSJ3231. The band for the sample obtained with the addition of 0.2 mM IPTG was more intense than the band for the sample obtained without the addition of IPTG.

These results show that the polypeptide expressed in *Escherichia coli* JM109 harboring pSJ3231 has an activity of digesting starch.

(2) Identification of Product Resulting from Hydrolysis of Starch by the Action of Expressed Polypeptide Before examining, an expressed polypeptide solution was prepared as follows.

*Escherichia coli* JM109 harboring pSJ3231 was inoculated into 20 ml of LB medium containing 100 µg/ml of ampicillin and cultured at 37° C. overnight. The culture was inoculated into 1 liter of the same medium and cultured at 37° C. until the turbidity reached. $OD_{600}$=0.5. IPTG at a final concentration of 0.2 mM was added thereto. The cells were further cultured overnight. The cells were collected by centrifugation, suspended in 40 ml of 50 mM sodium acetate buffer (pH 5.5), sonicated and treated at 80° C. for 10 minutes. Then, a supernatant was obtained by centrifugation.

Ammonium sulfate was added to the supernatant to 60% saturation. The mixture was stirred at 4° C. overnight. Precipitates collected by centrifugation were dissolved in 1 ml of the acetate buffer and dialyzed against the same buffer. Precipitates obtained after the dialysis was suspended in 200 µl of the buffer. The suspension was used as an expressed polypeptide suspension in the subsequent experiments.

The activity of hydrolyzing starch of the expressed polypeptide was identified as follows. Specifically, the expressed polypeptide suspension was allowed to act on various substrates. Products were then identified on thin-layer chromatography.

20 µl of an aqueous solution containing soluble starch (Nacalai Tesque) at a concentration of 5% or a suspension containing amylose (Nacalai Tesque) at concentration of 5% in water, 20 µl of the expressed polypeptide suspension, 10 µl of 500 mM sodium acetate buffer (pH 5.5) and 50 µl of water were mixed together. The mixture was reacted at 80° C. for 17 hours. 2 µl of the reaction mixture was subjected to silica gel thin-layer chromatography using Silica Gel 60F254 (Merck) as a thin layer plate and ethanol: 1-butanol: water=5:5:3 as a developing solvent. An orcinol-sulfuric acid reagent [prepared by dissolving 400 mg of orcinol (Sigma) in 22.8 ml of sulfuric acid and thereto adding water to make the total volume up to 200 ml] or a silver nitrate-ammonium reagent (a mixture of equal volumes of 0.1 M silver nitrate and 5 N aqueous ammonium) was sprayed to the thin layer plate after development and the plate was heated on a hot plate to observe the spots in order to confirm the products from the substrates.

As a result, glucose was generated by the action of the expressed polypeptide using either soluble starch or amylose as a substrate. Glucose was not observed for control experiments in which the expressed polypeptide or the substrate was used alone.

A reaction was carried out in a similar manner as described above except that a substrate which had been reduced using sodium boron hydride was used and that the reaction time was 0, 1, 3, 5.5 or 23 hours. The substrate was reduced as follows. 200 mg of starch or amylose was suspended in 1 ml of water and dissolved by heating. The solution was diluted to a volume of 4.5 ml. The resulting solution was cooled on ice. 0.5 ml of ice-cold 1.5% sodium boron hydride aqueous solution was slowly added thereto. The resulting mixture was reacted at 25° C. for 1 hour. 0.1 ml of acetone was added thereto. The mixture was allowed to stand at room temperature for 20 minutes and then neutralized using 1 N acetic acid. The resulting mixture was used as a substrate solution.

The amount of reducing sugar contained in this reaction mixture was measured according to the Park & Johnson method. Briefly, 10 μl of the reaction mixture which had been appropriately diluted, 40 μl of water, 50 μl of a carbonate cyanide solution and 50 μl of 0.05% potassium ferricyanide aqueous solution were mixed together and reacted for 15 minutes in boiling water bath. The carbonate cyanide solution was prepared by dissolving 5.3 g of sodium carbonate and 0.65 g of potassium cyanide in 1 liter of water. 75 μl of the reaction mixture was mixed with 125 μl of an iron alum solution. The iron alum solution was prepared by dissolving 1.5 g of iron alum and 1 g of SDS in 1 liter of 0.15 N sulfuric acid. The resulting mixture was allowed to stand at room temperature for 15 minutes. Absorbance at 690 nm was then measured. The amount of reducing end was determined as the amount of corresponding glucose based on a calibration curve prepared using glucose at a known concentration. In addition, the amount of glucose in the reaction mixture was measured using Glucose Test Wako (Wako Pure Chemical Industries).

As a result, the amounts of reducing sugar and glucose were increased with the lapse of reaction time. Thus, it was demonstrated that the polypeptide of the present invention has a glucoamylase activity.

Example 3

Enzymological Properties of Polypeptide (1) Preparation of Crude Extract

*Escherichia coli* JM109 harboring pSJ3231 was inoculated into 20 ml of LB medium containing 100 μg/ml of ampicillin and cultured at 37° C. overnight. The culture was inoculated into 1 liter of the same medium and cultured with shaking at 37° C. until the turbidity reached $OD_{600}$=0.5. IPTG at a final concentration of 0.2 mM was added thereto. The cells were further cultured overnight. The cells were collected by centrifugation, suspended in 75 ml of 50 mM sodium acetate buffer (pH 5.5) and sonicated. A supernatant obtained by centrifuging the sonicated suspension was treated at 80° C. for 10 minutes. The resulting insoluble substances were removed by centrifugation to obtain a supernatant. Ammonium sulfate was added to the supernatant to 60% saturation. The mixture was stirred at 4° C. for 5 hours. Precipitates obtained by centrifugation were suspended in 1 ml of the sodium acetate buffer and dialyzed overnight against the same buffer. A supernatant obtained by centrifugation was used as a crude extract in the subsequent experiments.

(2) Dependency Upon Reaction Temperature

Maltotriose (final concentration of 1%), $CaCl_2$ (final concentration of 1 mM) and the sodium acetate buffer (final concentration of 50 mM) were added to 10 μl of the crude extract prepared in Example 3-(1), and the total volume was made up to 50 μl. The mixture was reacted at 40, 60, 70, 80, 85, 90, 95 or 100° C. for 1 hour. The glucoamylase activity of the polypeptide of the present invention was determined by measuring the amount of glucose in the reaction mixture using Glucose Test Wako. As a result, the polypeptide of the present invention exhibited the maximal glucoamylase activity at 85 to 90° C.

The results are shown in FIG. 1. FIG. 1 illustrates the relationship between the glucoamylase activity of the polypeptide of the present invention and the reaction temperature. The horizontal axis represents the reaction temperature (° C.) and the vertical axis represents the glucoamylase activity (relative value, %).

(3) Dependency Upon Reaction pH

Maltotriose (final concentration of 1%) and a buffer (sodium acetate, MES-NaOH, sodium phosphate, Tris-HCl or glycine-NaOH; final concentration of 50 mM) were added to 10 μl of the crude extract prepared in Example 3-(1), and the total volume was made up to 50 μl. The mixture was reacted at 80 C for 1 hour. The pH of each buffer was adjusted at 80 C. The glucoamylase activity of the polypeptide of the present invention was determined by measuring the amount of glucose in the reaction mixture using Glucose Test Wako. As a result, the polypeptide of the present invention exhibited maximum glucoamylase activity at 5 to 6.

Figure 2:
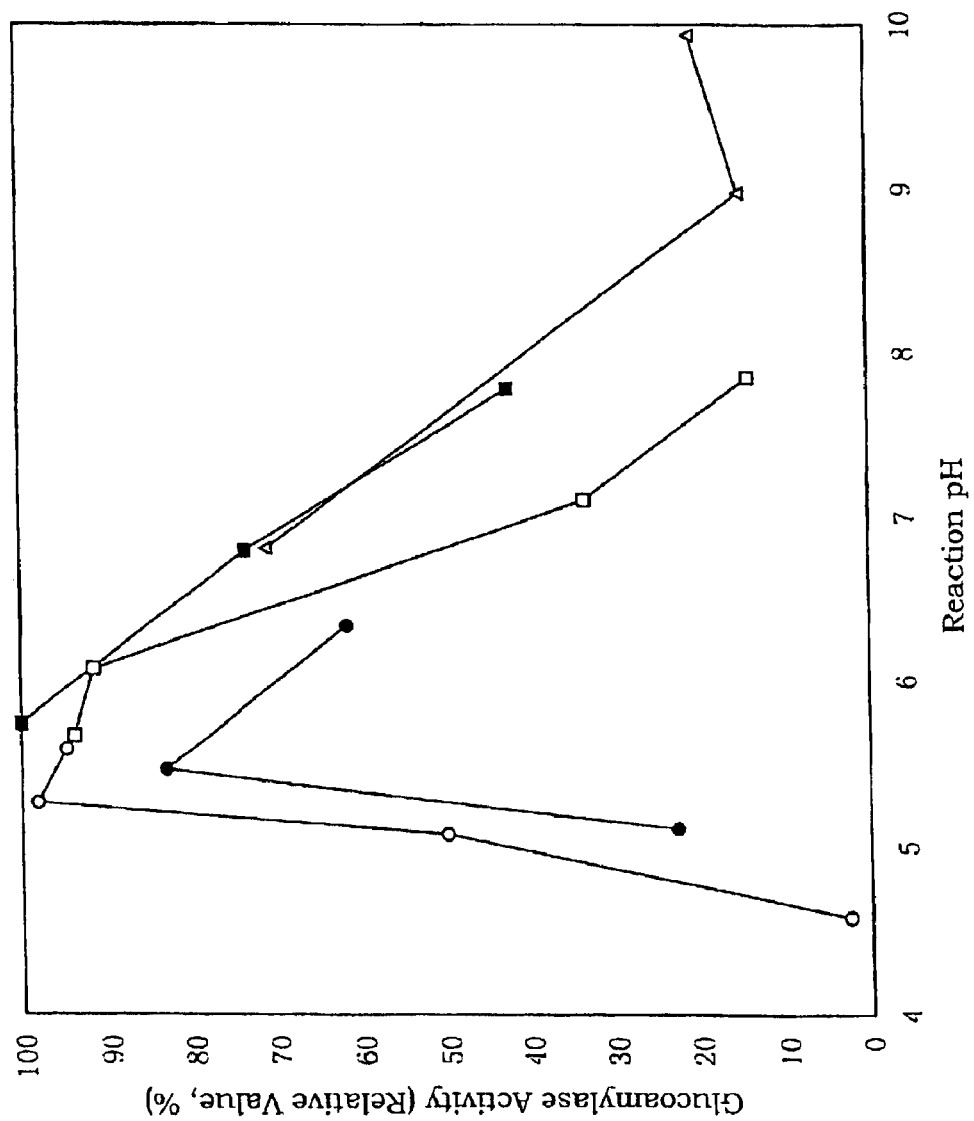
FIG. 2 illustrates the relationship between the reaction pH and the glucoamylase activity of the polypeptide of the present invention.

The results are shown in FIG. 2. FIG. 2 illustrates the relationship between the glucoamylase activity of the polypeptide of the present invention and the reaction pH. The horizontal axis represents the reaction pH and the vertical axis represents the glucoamylase activity (relative value, %). In FIG. 2, open circles (○), closed circles (●), open squares (□), closed squares (■) and open triangles (Δ) represent the results for sodium acetate buffers, MES-NaOH buffers, sodium phosphate buffers, Tris-HCl buffers and glycine-NaOH buffers, respectively.

(4) Heat Stability

An equal volume of 50 mM sodium acetate buffer (pH 5.5), the same buffer containing 2 mM EDTA or the same buffer containing 2 mM $CaCl_2$ was added to the crude extract prepared in Example 3-(1). The mixture was heated at 80 or 95° C. for 1, 5 or 24 hours. Maltotriose (final concentration of 1%), the sodium acetate buffer (final concentration of 50 mM) and $CaCl_2$ (final concentration of 1 mM) were added to 30 μl of the heated mixture, and the total volume was made up to 50 μl. The mixture was reacted at 80° C. for 1 hour. The remaining activity relative to the crude extract without the heat treatment was determined by measuring the amount of glucose in the reaction mixture using Glucose Test Wako. As a result, almost no inactivation was observed when the crude extract was heated at 80° C. in the absence of EDTA for 24 hours. When the crude extract was heated at 95° C., most of the activity was lost after heating for 1 hour without the addition of CaCl$_2$. On the other hand, with the addition of CaCl$_2$ at a concentration of 1 mM, no Inactivation was observed after heating for 5 hours and a slight remaining activity was observed after heating for 24 hours.

Figure 3:
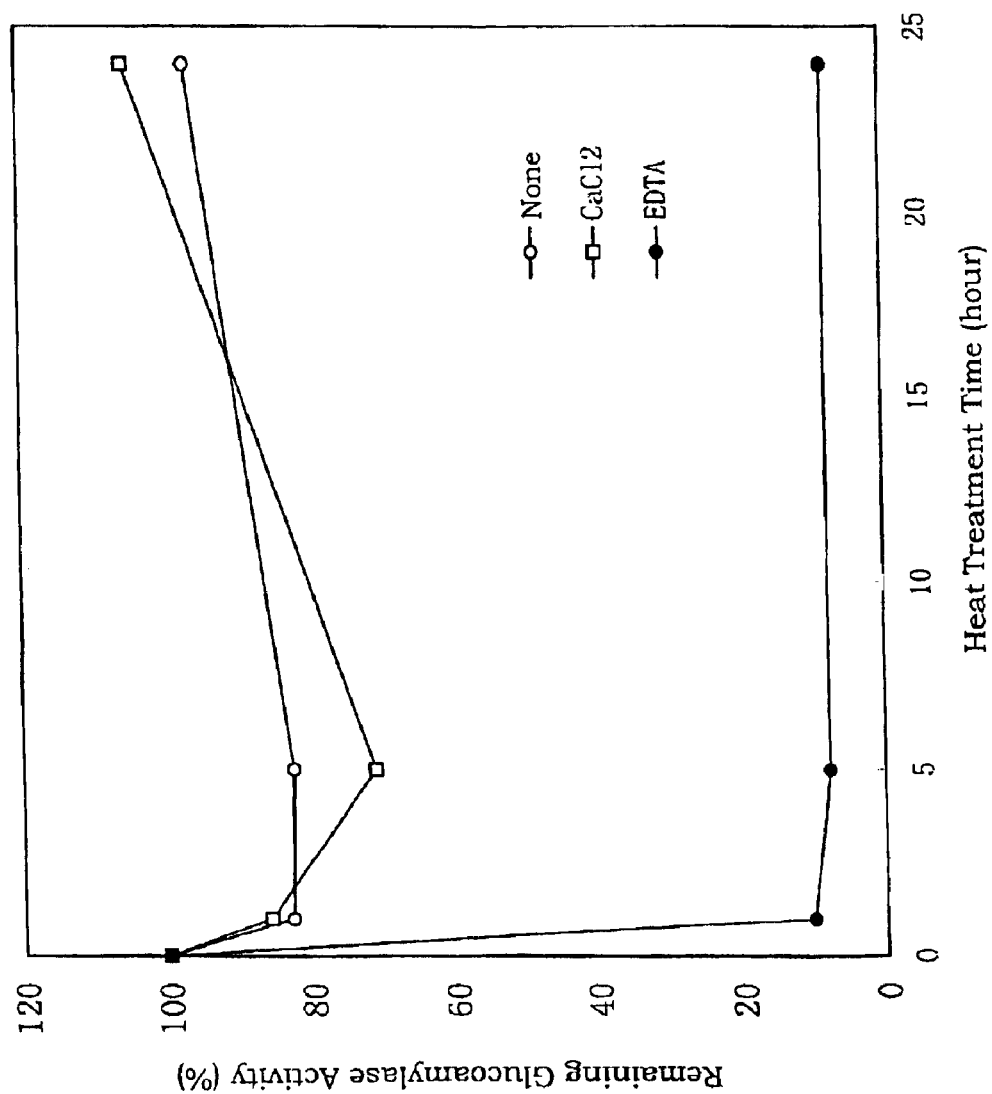
FIG. 3 illustrates the remaining glucoamylase activity of the polypeptide of the present invention upon heating at 80° C.
Figure 4:
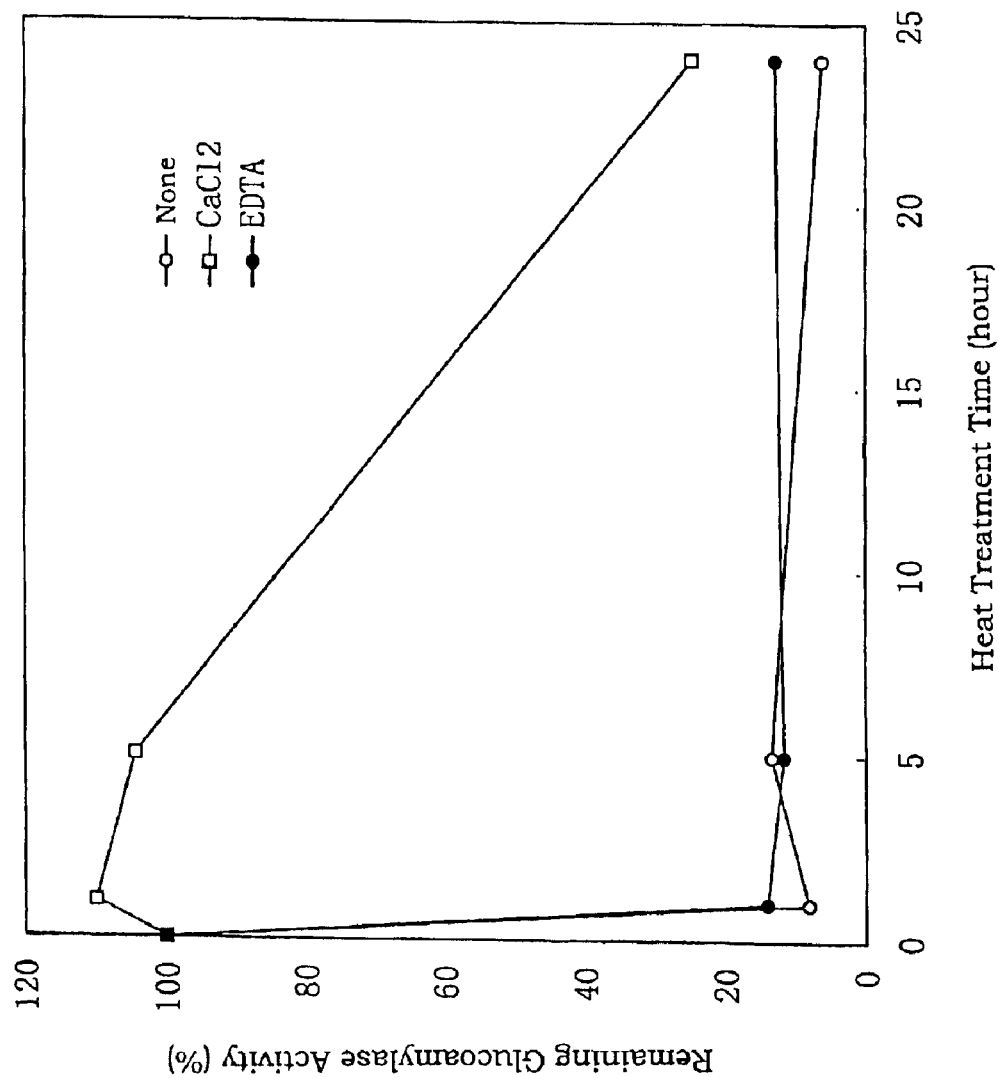
FIG. 4 illustrates the remaining glucoamylase activity of the polypeptide of the present invention upon heating at 95° C.

The results are shown in FIGS. 3 and 4. FIGS. 3 and 4 illustrate the remaining glucoamylase activity of the polypeptide of the present invention upon heating at 80° C. and 95° C., respectively. The horizontal axes represent the heat treatment time (hour) and the vertical axes represent the remaining glucoamylase activity (%). In FIGS. 3 and 4, open circles (○), closed circles (●) and open squares (□) represent the results for the heat treatment without the addition of EDTA or CaCl$_2$, the heat treatment with the addition of 1 mM EDTA and the heat treatment with the addition of 1 mM CaCl$_2$, respectively.

Additionally, when a remaining activity was determined after heating at 95° C. for 24 hours in the presence of 10 mM CaCl$_2$ in a similar manner as described above, almost 100% of the activity was retained.

(5) pH Stability

20 μl of 100 mM buffer (sodium acetate, MES-NaOH, sodium phosphate, Tris-HCl or glycine-NaOH) was added to 20 μl of the crude extract prepared in Example 3-(1). The mixture was heated at 80° C. for 10 minutes. Maltotriose (final concentration of 1%) and the sodium acetate buffer (final concentration of 50 mM) were added to 30 μl of the heated mixture, and the total volume was made up to 50 μl. The mixture was reacted at 80° C. for 1 hour. The remaining activity relative to the crude extract without the heat treatment was determined by measuring the amount of glucose in the reaction mixture using Glucose Test Wako. As a result, 50% or more of the activity remained after heating at pH 5 to 9.

(6) Effects of Metal Ions

Maltotriose (final concentration of 1%), the sodium acetate buffer (pH 5.5, final concentration of 50 mM) and CoCl$_2$, CaCl$_2$, CuSO$_4$, FeCl$_3$, ZnCl$_2$, MgCl$_2$ or EDTA (final concentration of 0, 0.5, 1, 2 or 10 mM) were added to 10 μl of the crude extract prepared in Example 3-(1), and the total volume was made up to 50 μl. The mixture was reacted at 80° C. for 1 hour. The glucoamylase activity of the polypeptide of the present invention was determined by measuring the amount of glucose in the reaction mixture using Glucose Test Wako. As a result, the glucoamylase activity of the polypeptide of the present invention was not significantly influenced by CoCl$_2$, CaCl$_2$, FeCl$_3$ or MgCl$_2$ at a concentration of 0.5, 1, 2 or 10 mM. The activity was completely inhibited by CuSO$_4$ or ZnCl$_2$ at a concentration of 2 mM, or EDTA at a concentration of 0.5 mM.

Figure 5:
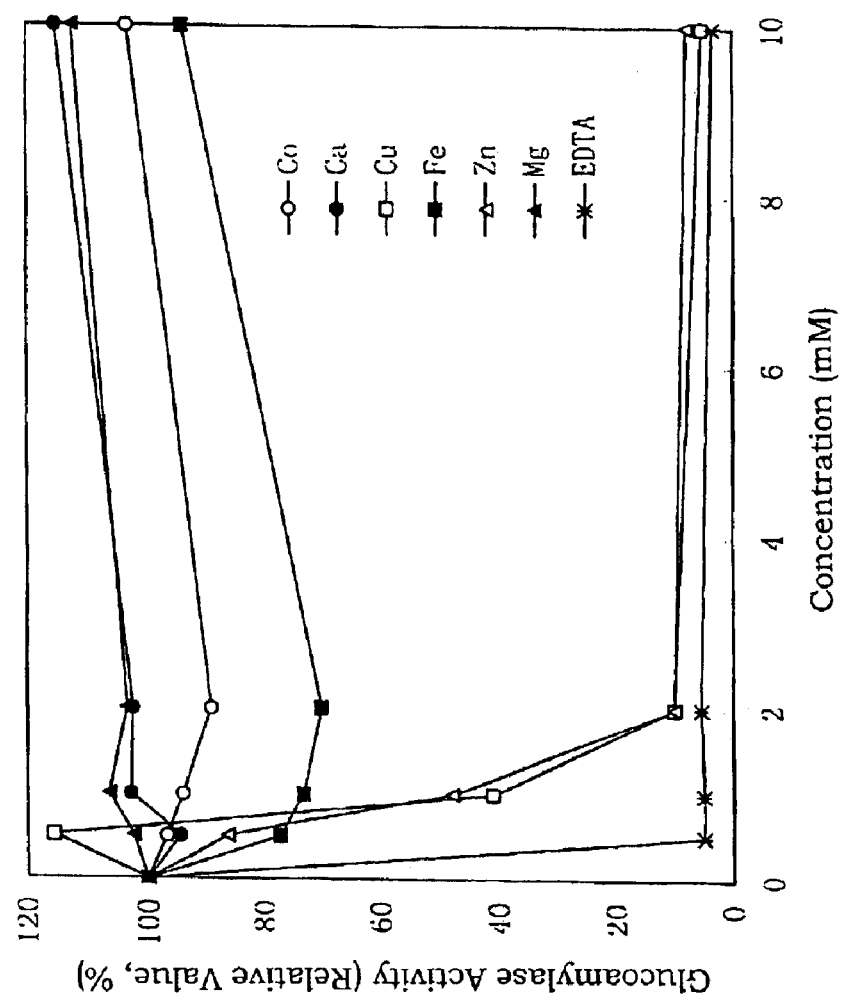
FIG. 5 illustrates the relationship between the concentration of a metal ion or EDTA and the glucoamylase activity of the polypeptide of the present invention.

The results are shown in FIG. 5. FIG. 5 illustrates the relationship between the concentration of a metal ion or EDTA and the glucoamylase activity of the polypeptide of the present invention. The horizontal axis represents the concentration of the metal ion or EDTA added and the vertical axis represents the glucoamylase activity (relative value, %). In FIG. 5, open circles (○), closed circles (●), open squares (□), closed squares (■), open triangles (△), closed triangles (▲) and asterisks (*) represent the results for the addition of CoCl$_2$, CaCl$_2$, CuSO$_4$, FeCl$_3$, ZnCl$_2$, MgCl$_2$ and EDTA, respectively.

Example 4

Properties of Mutant Polypeptides (1) Construction of Recombinant Plasmid pET21amyCΔS An oligonucleotide PX253-01 having a nucleotide sequence of SEQ ID NO:8 and an oligonucleotide R4 having a nucleotide sequence of SEQ ID NO:9 were synthesized. A PCR was carried out using these two oligonucleotides as primers and pSJ3231 as a template. The PCR was carried out according to the protocol attached to TaKaRa ExTaq as follows: 30 cycles of 94° C. for 0.5 minute, 55° C. for 0.5 minute and 72° C. for 2 minutes. A DNA was recovered from the reaction mixture by ethanol precipitation, digested with NcoI and EcoRI (both from Takara Shuzo) and then subjected to agarose gel electrophoresis. An about 1.0-kb DNA fragment was extracted and purified from the gel. The DNA fragment was ligated to pET21d (Novagen) digested with NcoI and EcoRI using T4 DNA ligase. The ligation mixture was used to transform *Escherichia coli* JM109. Plasmids were prepared from the resulting transformants to obtain pRH03. The about 1.0-kb DNA fragment was inserted into pRH03. When the nucleotide sequence was determined, it was shown that the fragment contained a sequence CCATGG recognized by NcoI followed by a sequence from C at position 2 to C at position 1048 in the nucleotide sequence of SEQ ID NO:7.

The about 3.5-kb amplified DNA fragment prepared in Example 1-(2) was digested with AflII and SacI (both from Takara Shuzo) and subjected to agarose gel electrophoresis. An about 1.8-kb DNA fragment was extracted and purified from the gel. This DNA fragment was ligated to pRH03 digested with AflII and SacI using T4 DNA ligase. The ligation mixture was used to transform *Escherichia coli* JM109. Plasmids were prepared from the resulting transformants to obtain pET21amyCΔS . When the nucleotide sequence of pET21amyCΔS was determined, it was shown that the plasmid has a polynucleotide having a nucleotide sequence of SEQ ID NO:7, and the nucleotide sequence encodes a polypeptide having an amino acid sequence of SEQ ID NO:6.

(2) Construction of Expression Plasmids for Mutant Polypeptides

The following oligonucleotides were synthesized: an oligonucleotide F206S-F having a nucleotide sequence of SEQ ID NO:10; an oligonucleotide F206S-R having a nucleotide sequence of SEQ ID NO:11; an oligonucleotide P142I-F having a nucleotide sequence of SEQ ID NO:12; an oligonucleotide P142I-R having a nucleotide sequence of SEQ ID NO:13; an oligonucleotide L337V-F having a nucleotide sequence of SEQ ID NO:14; an oligonucleotide L337V-R having a nucleotide sequence of SEQ ID NO: 15; an oligonucleotide F2 having a nucleotide sequence of SEQ ID NO:16; an oligonucleotide F3 having a nucleotide sequence of SEQ ID NO:17; an oligonucleotide AN2-R1F2 having a nucleotide sequence of SEQ ID NO:18; an oligonucleotide R5 having a nucleotide sequence of SEQ ID NO:19; and an oligonucleotide R6 having a nucleotide sequence of SEQ ID NO:20.

PCRs were carried out using pSJ3231 as a template and the oligonucleotides as shown in Table 1 as primers. The PCRs were carried out according to the protocol attached to TaKaRa ExTaq as follows: 20 cycles of 94° C. for 0.5 minute, 55° C. for 0.5 minute and 72° C. for 1 minute. The PCR reaction mixtures were subjected to agarose gel electrophoresis. DNA fragments each having the chain length as shown in Table 1 were extracted and purified from the gel.

TABLE 1

| Reaction | FS-F | FS-R | PI-F | PI-R | LV-F | LV-R |
|---|---|---|---|---|---|---|
| Primer 1 | F206 S-F | F206 S-R | P142 I-F | P142 I-R | L337 V-F | L337 V-R |
| Primer 2 | R5 | F2 | R6 | AN2-R1F2 | R4 | F3 |
| Chain length (bp) | about 400 | about 260 | about 290 | about 260 | about 300 | about 350 |

Amplified DNA fragments purified as described above were used for PCRs as follows. PCRs were further carried out using the combinations of the purified DNA fragments as templates and the primers as shown in Table 2. "Template 1" and "template 2" indicated in Table 2 correspond to "reaction" in Table 1, indicating that the DNA fragments from the reactions shown in Table 1 were used in the reactions shown in Table 2 as templates. The PCRs were carried out according to the protocol attached to TaKaRa ExTaq as follows: 10 cycles of 94° C. for 0.5 minute, 55° C. for 0.5 minute and 72° C. for 1 minute. The PCR reaction mixtures were subjected to agarose gel electrophoresis. DNA fragments each having the chain length as shown in Table 2 were extracted and purified from the gel.

TABLE 2

| Reaction | FS | PI | LV |
|---|---|---|---|
| Template 1 | FS-F | PI-F | LV-F |
| Template 2 | FS-R | PI-R | LV-R |
| Primer 1 | F2 | AN2-R1F2 | F3 |
| Primer 2 | R5 | R6 | R4 |
| Chain length (bp) | about 650 | about 530 | about 640 |

The DNA fragment from the reaction FS in Table 2 was digested with AflII and NdeI (Takara Shuzo) and subjected to agarose gel electrophoresis. An about 320-bp DNA fragment was extracted and purified from the gel. This fragment was ligated to pET21amyCΔS digested with AflII and NdeI using T4 DNA ligase. The ligation mixture was used to transform *Escherichia coli* JM109. Plasmids were prepared from the resulting transformants to obtain pamyCΔS-F206S. When the nucleotide sequence of pamyCΔS-F206S DNA was determined, it was shown that the plasmid encodes a polypeptide having an amino acid sequence of SEQ ID NO:6 in which Phe at position 187 (corresponding to position 206 in the amino acid sequence of SEQ ID NO:1) is replaced by Ser. This mutant polypeptide was designated as F206S.

The DNA fragment from the reaction PI in Table 2 was digested with BalI (Takara Shuzo) and AflII and subjected to agarose gel electrophoresis. An about 280-bp DNA fragment was extracted and purified from the gel. This fragment was ligated to pET21amyCΔS digested with BalI and AflII using T4 DNA ligase. The ligation mixture was used to transform *Escherichia coli* JM109. Plasmids were prepared from the resulting transformants to obtain pamyCΔS-P142I. When the nucleotide sequence of pamyCΔS-P142I DNA was determined, it was shown that the plasmid encodes a polypeptide having an amino acid sequence of SEQ ID NO:6 in which Pro at position 123 (corresponding to position 142 in the amino acid sequence of SEQ ID NO:1) is replaced by Ile. This mutant polypeptide was designated as P142I.

The DNA fragment from the reaction LV in Table 2 was digested with NdeI and EcoRI and subjected to agarose gel electrophoresis. An about 170-bp DNA fragment was extracted and purified from the gel. This fragment was ligated to pET21amyCΔS digested with NdeI and EcoRI using T4 DNA ligase. The ligation mixture was used to transform *Escherichia coli* JM109. Plasmids were prepared from the resulting transformants to obtain pamyCΔS-L337V. When the nucleotide sequence of pamyCΔS-L337V DNA was determined, it was shown that the plasmid encodes a polypeptide having an amino acid sequence of SEQ ID NO:6 in which Leu at position 318 (corresponding to position 337 in the amino acid sequence of SEQ ID NO:1) is replaced by Val. This mutant polypeptide was designated as L337V.

(3) Production of Wild Type and Mutant Polypeptides

*Escherichia coli* BL21(DE3) (Novagen) was transformed with pET21amyCΔS, pamyCΔS-F206S, pamyCΔS-P142I or pamyCΔS-L337V. Each of the resulting transformants was inoculated into 20 ml of LB medium containing 100 μg/ml of ampicillin and cultured aerobically at 37° C. overnight. After cultivation, the cells were collected by centrifugation, suspended in 0.8 ml of 50 mM sodium acetate buffer (pH 5.5), disrupted by sonication and treated at 80° C. for 30 minutes. A supernatant obtained by centrifugation was used as a crude extract. Hereinafter, crude extracts from *Escherichia coli* BL21(DE3) transformed with pET21amyCΔS, pamyCΔS-F206S, pamyCΔS-P142I and pamyCΔS-L337V are referred to as a crude extract WT, a crude extract F206S, a crude extract P142I and a crude extract L337V, respectively.

(4) Digestion of Maltooligosaccharides with Wild Type and Mutant Polypeptides

Maltotriose (final concentration of 1%), sodium acetate buffer (pH 5.5, final concentration of 50 mM) and CaCl$_2$ (final concentration of 1 mM) were added to 5 μl of one of the crude extracts obtained in Example 4-(3), and the total volume was made up to 50 μl. The mixture was reacted at 80° C. for 1 hour. The glucoamylase activity of the polypeptide of the present invention contained in the crude extract was determined by measuring the amount of glucose in the reaction mixture using Glucose Test Wako. As a result, provided that the glucoamylase activity for the crude extract WT was defined as 1, the glucoamylase activities for the crude extract F206S, the crude extract P142I and the crude extract L337V were determined to be 2.08, 0.55, and 0.30, respectively.

Similar reactions were carried out using maltopentaose in place of maltotriose. As a result, provided that the glucoamylase activity for the crude extract WT was defined as 1, the glucoamylase activities for the crude extract F206S, the crude extract P142I and the crude extract L337V were determined to be 1.92, 0.53, and 0.37, respectively.

Figure 6:
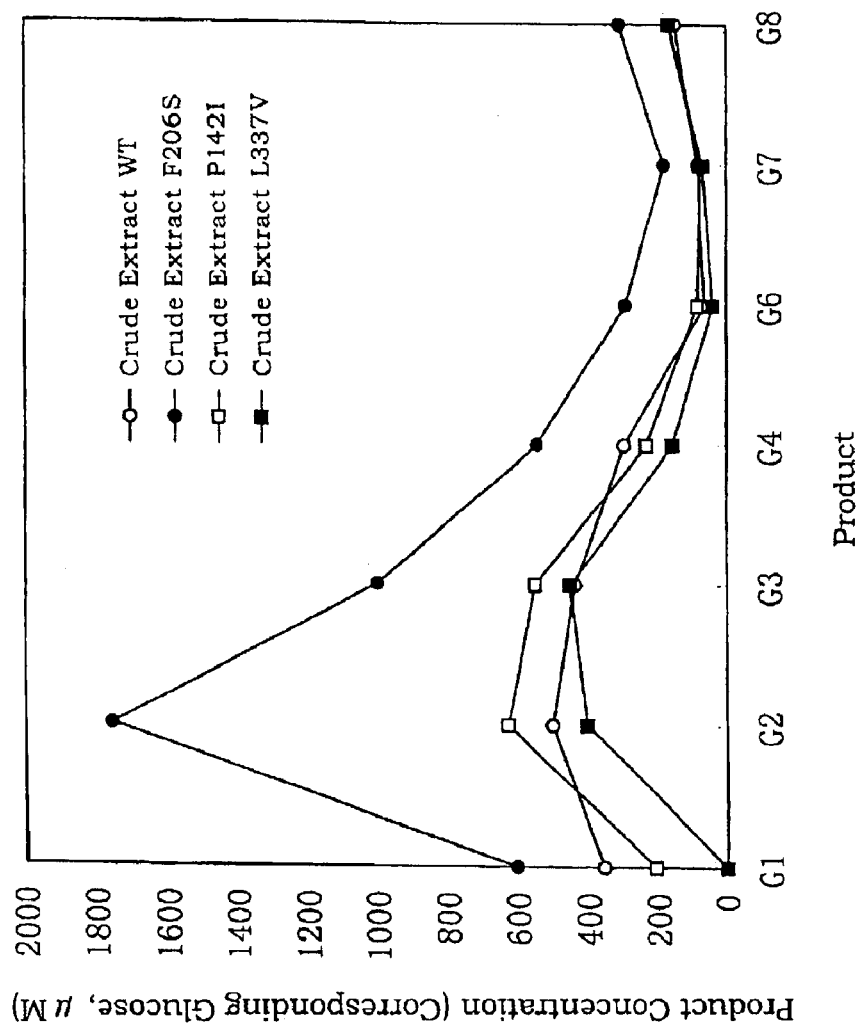
FIG. 6 illustrates the composition of products obtained by allowing respective crude extracts to act on maltopentaose.

65 μl of acetonitrile was added to and mixed with 35 μl of the reaction mixture obtained as described above using maltopentaose as a substrate. The mixture was centrifuged to remove insoluble substances. The composition of oligosaccharides contained in the sample was analyzed by normal phase HPLC using Palpak Type S (Takara Shuzo). 65% acetonitrile aqueous solution was used for the mobile phase. The flow rate was 1 ml/minute and the column temperature was 40° C. Detection was carried out using a differential refractive index detector Shodex RI-71 (Showa Denko). 65 μl of acetonitrile was added to 35 μl of each of aqueous solution containing glucose (Nacalai Tesque), maltose, maltotriose, maltopentaose or maltoheptaose (Seikagaku Corporation) at a concentration of 0.1%. Supernatants obtained by centrifuging the mixtures were used as standards. The retention times for the standards were as follows: 5.6 minutes (glucose), 7.3 minutes (maltose), 9.7 minutes (maitotriose), 17.8 minutes (maltopentaose) arid 30.7 minutes (maltoheptaose). As a result, it was shown that maltooligosaccharides having degrees of polymerization ranging from 1 to 8 were generated when the respective crude extracts were allowed to act on maltopentaose. The results are shown in FIG. 6. FIG. 6 illustrates the composition of products obtained by allowing the respective crude extracts to act on maltopentaose. The horizontal axis represents the products (G1: glucose; G2: maltose; G3: maltotriose; G4: maltotetraose; G6: maltohexaose; G7: maltoheptaose; and G8: maltooctaose) and the vertical axis represents the concentration of the product (as the concentration of corresponding glucose; $\mu$M) in the reaction mixture. In FIG. 6, open circles (○), closed circles (●), open squares (□) and closed squares (■) represent the results for the crude extract WT, the crude extract F206S, the crude extract P142I and the crude extract L337V, respectively. The amounts of generated glucose determined using HPLC as described above are not consistent with the results obtained using Glucose Test Wako. It is considered that this is because a peak for the solvent appeared at the position at which glucose was eluted in HPLC, and thus the measurement for glucose included an error.

(5) Digestion of Starch with Wild Type and Mutant Polypeptides

Figure 7:
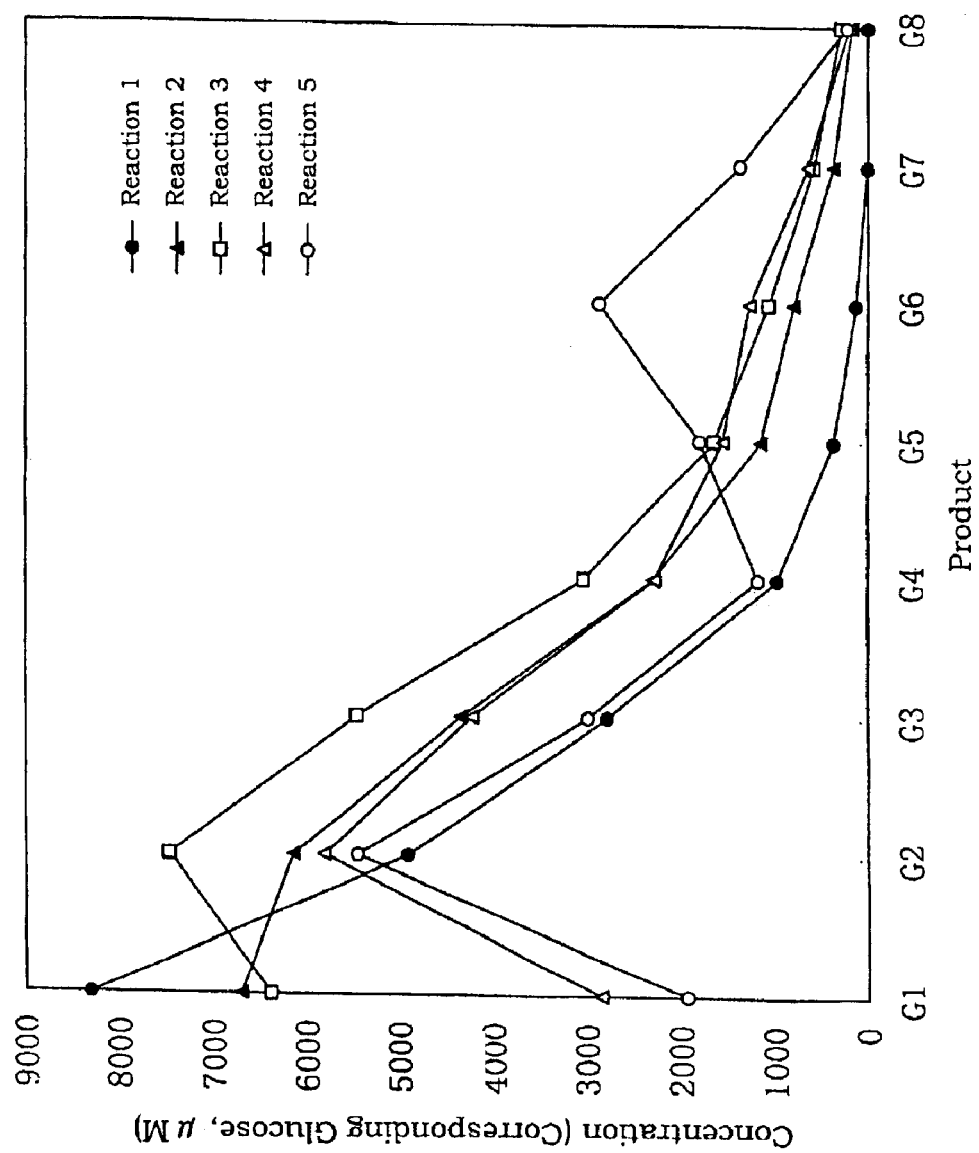
FIG. 7 illustrates the composition of products obtained by allowing respective crude extracts to act on soluble starch.

A hyperthermostable $\alpha$-amylase preparation was prepared according to a method as described in Example 3 of JP-A 7-143880 entitled "Hyperthermostable $\alpha$-amylase gene." The following volumes of the crude extract F206S and the hyperthermostable $\alpha$-amylase preparation were used: 40 $\mu$l and 0 $\mu$l (reaction 1); 30 $\mu$l and 10 $\mu$l (reaction 2); 20 $\mu$l and 20 $\mu$l (reaction 3); 10 $\mu$l and 30 $\mu$l (reaction 4); and 0 $\mu$l and 40 $\mu$l (reaction 5). Soluble starch (Nacalai Tesque; final concentration of 2%), sodium acetate buffer (pH 5.5; final concentration of 50 mM) and $CaCl_2$ (final concentration of 1 mM) were added thereto, and the total volume was made up to 200 $\mu$l. The mixture was reacted at 80° C. overnight. The oligosaccharides in the reaction mixtures were analyzed by normal HPLC as described in Example 4-(4). As compared with the results obtained by using the hyperthermostable $\alpha$-amylase preparation or the crude extract F206S alone, the sum of the concentrations (as the concentrations of corresponding glucose) of glucose, maltose and maltotriose, which can be fermented by a yeast commonly used for alcohol fermentation, was greater when these enzymes were used in combination. The results are shown in FIG. 7. FIG. 7 illustrates the composition of products obtained by allowing the respective crude extracts to act on soluble starch. The horizontal axis represents the products (G5: maltopentaose; others are described above for FIG. 6) and the vertical axis represents the concentration of the product in the reaction mixture (as the concentration of corresponding glucose; $\mu$M). In FIG. 7, open circles (○), open triangles (△), open squares (□), closed triangles (▲) and closed circles (●) represent the results for the reaction 1, the reaction 2, the reaction 3, the reaction 4 and the reaction 5, respectively.

(6) Activity of Synthesizing Cyclodextrin of the Polypeptide of the Present Invention 2 units of glucoamylase from *Aspergillus niveus* (Seikagaku Corporation) were added to 50 $\mu$l of the reaction mixture of the reaction 1 in Example 4-(5). The mixture was reacted at 37° C. for 3 hours. When the reaction mixture was analyzed by normal phase HPLC as described in Example 4-(4), peaks having the same retention times as those observed for $\alpha$-cyclodextrin (CD), $\beta$-CD and $\gamma$-CD (Seikagaku Corporation) were observed. The retention times for $\alpha$-CD, $\beta$-CD and $\gamma$-CD were 12.3 minutes, 15.2 minutes and 19.7 minutes, respectively. The fractions corresponding to these peaks were collected and subjected to mass spectrometry in the positive ion mode using a triple stage quadrupole mass spectrometer API 300 (Perkin-Elmer Sciex) As a result, the samples from the respective peaks resulted in the same mass spectra as those of $\alpha$-CD, $\beta$-CD and $\gamma$-CD. Thus, it was shown that the polypeptide of the present invention contained in the crude extract F206S has an activity of synthesizing CD.

(7) Construction of Expression Plasmids for Double-mutant Polypeptides pamyC$\Delta$S-F206S was digested with PstI (Takara Shuzo) and AflII, and subjected to agarose gel electrophoresis. An about 3.1-kb DNA fragment was extracted and purified from the gel to obtain a DNA 1. pamyC$\Delta$S-P142I was digested with PstI and AflII, and subjected to agarose gel electrophoresis. An about 4.6-kb DNA fragment was extracted and purified from the gel to obtain a DNA 2. pamyC$\Delta$S-F206S was digested with PstI and NdeI, and subjected to agarose gel electrophoresis. An about 4.9-kb DNA fragment was extracted and purified from the gel to obtain a DNA 3. pamyC$\Delta$S-L337V was digested with PstI and NdeI, and subjected to agarose gel electrophoresis. An about 2.8-kb DNA fragment was extracted and purified from the gel to obtain a DNA 4.

The DNA 1 and the DNA 2 were ligated each other using T4 DNA ligase. The ligation mixture was used to transform *Escherichia coli* HB101 (Takara Shuzo). A plasmid pamyC$\Delta$S-F206S/P142I was obtained from a transformant. When the nucleotide sequence of the pamyC$\Delta$S-F206S/P142I DNA was determined, it was shown that the plasmid encodes a polypeptide having an amino acid sequence of SEQ ID NO:6 in which Phe at position 187 is replaced by Ser and Pro at position 123 is replaced by Ile. This mutant polypeptide was designated as FS/PI.

The DNA 3 and the DNA 4 were ligated each other using T4 DNA ligase. The ligation mixture was used to transform *Escherichia coli* HB101. A plasmid pamyC$\Delta$S-F206S/L337V was obtained from a transformant. When the nucleotide sequence of the pamyC$\Delta$S-F206S/L337V DNA was determined, it was shown that the plasmid encodes a polypeptide having an amino acid sequence of SEQ ID NO:6 in which Phe at position 187 is replaced by Ser and Leu at position 318 is replaced by Val. This mutant polypeptide was designated as FS/LV.

(8) Properties of Double-mutant Polypeptides

*Escherichia coli* BL21(DE3) was transformed with pamyC$\Delta$S-F206S/P142I or pamyC$\Delta$S-F206S/L337V. A crude extract FS/PI and a crude extract FS/LV were obtained using the transformants as described in Example 4-(3).

Soluble starch (final concentration of 2%), sodium acetate buffer (pH 5.5; final concentration of 50 mM) and $CaCl_2$ (final concentration of 1 mM) were added to 20 $\mu$l of the crude extract WT, the crude extract F206S (both prepared in Example 4-(3)), the crude extract FS/PI or the crude extract FS/LV, and the total volume was made up to 100 $\mu$l. The mixture was reacted at 80° C. overnight. The oligosaccharides in the reaction mixtures were analyzed by normal phase HPLC as described in Example 4-(4). As a result, provided that the sum of the concentrations (as the concentrations of corresponding glucose) of glucose, maltose and maltotriose for the crude extract WT was defined as 1, the values for the crude extract F206S, the crude extract FS/PI and the crude extract FS/LV were determined to be 2.22, 2.22, and 2.79, respectively.

Regarding the composition of produced CDs, the amount of γ-CD was about half the amount of β-CD when the crude extract WT was used. The amounts of γ-CD and β-CD were almost equivalent when the crude extract F206S or the crude extract FS/LV was used. The amount of γ-CD was about 1.7-fold more than that of β-CD when the crude extract FS/PI was used. The results are shown in Table 3.

TABLE 3

| Crude extract | Produced amount (μM) | |
|---|---|---|
| | β-CD | γ-CD |
| WT | 220 | 103 |
| F206S | 292 | 294 |
| FS/PI | 227 | 386 |
| FS/LV | 379 | 363 |

Industrial Applicability

The present invention provides a polypeptide having a glucoamylase activity. The polypeptide of the present invention is highly thermostable and can efficiently digest starch. Furthermore, it is possible to efficiently produce glucose from starch by using the polypeptide of the present invention in combination with an α-amylase from a hyperthermophile, facilitating the utilization of biomass.

Sequence Listing Free Text

SEQ ID NO:3: PCR primer am1-F1 for amplifying a gene encoding a polypeptide having a glucoamylase activity from *Pyrococcus furiosus*.

SEQ ID NO:4 PCR primer AMY-2N for amplifying a gene encoding a polypeptide having a glucoamylase activity from *Pyrococcus furiosus*.

SEQ ID NO:8: PCR primer PX253-01.
SEQ ID NO:9: PCR primer R4.
SEQ ID NO:10: PCR primer 206S-F.
SEQ ID NO:11: PCR primer F206S-R.
SEQ ID NO:12: PCR primer P142I-F.
SEQ ID NO:13: PCR primer P142I-R.
SEQ ID NO:14: PCR primer L337V-F.
SEQ ID NO:15: PCR primer L337V-R.
SEQ ID NO:16: PCR primer F2.
SEQ ID NO:17: PCR primer F3.
SEQ ID NO:18: PCR primerAN2-R1F2.
SEQ ID NO:19: PCR primer R5.
SEQ ID NO:20: PCR primer R6.

What is claimed is:

1. An isolated nucleic acid encoding a polypeptide having a thermostable glucoamylase activity selected from the group consisting of:
  (a) a nucleic acid encoding a polypeptide having the amino acid sequence of SEQ ID NO:6 or an amino acid sequence that differs from SEQ ID NO:6 by one to up to three amino acid substitution(s) selected from the group consisting of:
    i. substitution of Ser for Phe at position 187;
    ii. substitution of Ile for Pro at position 123;
    iii. substitution of Val for Leu at position 318;
  (b) a nucleic acid having the nucleotide sequence of SEQ ID NO:7.

2. A recombinant DNA containing the nucleic acid defined by claim 1.

3. A host cell transformed with the recombinant DNA defined by claim 2.

4. A method for producing a polypeptide having a thermostable glucoamylase activity, the method comprising culturing the host cell defined by claim 3 and collecting a polypeptide having a thermostable glucoamylase activity from the culture.

* * * * *

SEQUENCE LISTING

```
<160> NUMBER OF SEQ ID NOS: 20

<210> SEQ ID NO 1
<211> LENGTH: 722
<212> TYPE: PRT
<213> ORGANISM: Pyrococcus furiosus

<400> SEQUENCE: 1

Met Arg Lys Leu Ile Ile Ser Phe Thr Ile Leu Val Leu Tyr Phe Ser
1               5                   10                  15

Gln Val Ala Ala Tyr Tyr Val Pro Glu Arg Ser Val Ile Tyr Gln Ile
            20                  25                  30

Met Val Asp Arg Phe Tyr Asp Arg Asn Pro Thr Asn Asn Glu Pro Phe
        35                  40                  45

Tyr Asp Pro Glu Lys Lys Asn Tyr Arg Leu Tyr Trp Gly Gly Asp Ile
    50                  55                  60

Glu Gly Ile Ile Glu Arg Leu Asp Tyr Ile Glu Ser Leu Gly Val Ser
65                  70                  75                  80

Met Ile Trp Leu Ser Pro Leu Asn Asp Asn Ile Asn Arg Met Ala Gly
                85                  90                  95

Gly Ser Ala Pro Tyr His Gly Tyr Trp Pro Arg Asp Phe Lys Arg Ile
            100                 105                 110

Asp Glu His Phe Gly Thr Trp Glu Asp Phe Arg Arg Leu Val Glu Glu
        115                 120                 125

Ala Lys Lys Arg Gly Ile Cys Ile Ile Val Asp Tyr Val Pro Asn His
    130                 135                 140

Ser Asn Pro Ala Thr Asp Gly Glu Phe Gly Ala Leu Tyr Asp Asn Gly
145                 150                 155                 160

Thr Leu Val Thr Asn Tyr Tyr Glu Asp Arg Lys Asn Ala Thr Arg Asn
                165                 170                 175

Pro Tyr Thr Ala Ser Leu Glu Asn Ile Tyr His His Asn Gly Asn Ile
            180                 185                 190
```

-continued

```
Asn Asp Trp Phe Gly Phe Gln Leu Lys Tyr Ala Asn Leu Phe Gly Leu
        195                 200                 205

Ala Asp Phe Asn Gln Met Asn Asp Phe Val Asp Asn Tyr Leu Lys Glu
210                 215                 220

Gly Ala Ala Leu Phe Val Lys Asn Gly Ala Cys Gly Phe Arg Ile Asp
225                 230                 235                 240

Ala Val Lys His Ile Glu Leu Gly Trp Leu Glu Thr Phe Tyr Leu Tyr
                245                 250                 255

Leu Tyr Gln Ile Ser Asp Glu Pro Leu Phe Ile Tyr Gly Glu Tyr Phe
            260                 265                 270

Ala Asn Thr Pro Asp Lys Thr Phe Asp Leu Tyr Glu Phe Tyr Arg Tyr
            275                 280                 285

Ser Asn Val Ser Ser Leu Leu Asn Ile Pro Ile Arg Glu Ser Ile Ala
        290                 295                 300

Arg Thr Phe Ala Tyr Gly Gly Ser Phe Glu Gln Leu Ala Lys Met Leu
305                 310                 315                 320

Glu Glu Tyr Tyr Ser Leu Phe Val Tyr Pro Asn Lys Gln Leu Asn Phe
                325                 330                 335

Leu Asp Ser His Asp Leu Val Arg Phe Leu Asn Met Asn Pro Asn Lys
            340                 345                 350

Asp Arg Tyr His Met Ala Leu Gly Leu Val Met Thr Leu Pro Gly Ile
            355                 360                 365

Pro Val Ile Tyr Tyr Gly Asp Glu Ser Tyr Leu Val Ser Lys Glu Gly
        370                 375                 380

Lys Gly Asp Pro Tyr Asn Arg Pro Met Met Val Phe Asp Asn Ser Thr
385                 390                 395                 400

Lys Ala Ala Glu Ile Ile Arg Lys Leu Ser Leu Leu Arg Lys Val Asn
                405                 410                 415

Asp Ala Leu Ala Tyr Ser Asp Phe Arg Thr Val Tyr Val Asp Tyr Asn
            420                 425                 430

Thr Trp Ile Phe Glu Arg Lys Phe Gly Ser His Lys Ile Leu Val Ala
            435                 440                 445

Leu Asn Lys Gly Pro Asp Lys Asn Ile Thr Ile Ser Leu Asn Trp Thr
        450                 455                 460

Asp Gly Thr Tyr Ile Asp Ile Glu Gly Ala Ile Leu Lys Val Lys
465                 470                 475                 480

Glu Gly Gln Gly Glu Ile Lys Leu Pro Arg Tyr Ser Phe Tyr Val Phe
                485                 490                 495

His Val Glu Glu Gln Lys Thr Pro Leu Ile Gly Ser Ile Thr Pro
            500                 505                 510

Tyr Ile Ala Gln Pro Gly Gln Lys Ile Leu Ile Ala Gly Ala Gly Leu
            515                 520                 525

Asn Gly Asn Ile Lys Val Tyr Ile Gly Gly Arg Arg Ala Arg Ile Ile
        530                 535                 540

Glu Lys Glu Glu Asn Ser Ile Leu Val Glu Val Pro Glu Ile Lys Thr
545                 550                 555                 560

Met Asn Ala Trp Ile Pro Val Trp Val Val Asn Gly Thr Arg Ser
                565                 570                 575

Asn Glu Val Lys Leu Arg Tyr Tyr Ser Ser Asn Asp Ile Pro Ala Leu
            580                 585                 590

Ile Val Leu Gln Gly Asn Tyr Thr Gly Tyr Leu Trp Val Lys Gly Asn
        595                 600                 605

Ile Pro Glu Leu Ser Glu Pro Arg Pro Leu Leu Lys Ser Pro Thr Gly
```

```
                610                615                620
His Tyr Phe Ala Val Val Pro Leu Pro Arg Asn Lys Thr Phe Thr Val
625                630                635                640

Gln Leu Tyr Lys Gly Leu Pro Trp Glu Pro Leu Gln Pro Thr Asn Val
                645                650                655

Thr Leu Tyr Gly Ile Gly Asn Lys Thr Val Ile Leu Asn Glu Ala Ala
                660                665                670

Pro Glu Thr Pro Val Cys Gly Pro Gly Ile Val Ala Val Phe Ala Leu
                675                680                685

Leu Pro Leu Leu Lys Arg Lys Lys Lys Ser Pro Asn Thr Thr Ile
                690                695                700

Thr Pro Tyr Gly Val Pro Ile Val Ala Val Ser Trp Ile Val Arg Trp
705                710                715                720

Cys Leu

<210> SEQ ID NO 2
<211> LENGTH: 2169
<212> TYPE: DNA
<213> ORGANISM: Pyrococcus furiosus

<400> SEQUENCE: 2
atgagaaagc tgataataag ttttacaatt cttgtactct attttttccca ggtcgcagcc      60
tattatgttc cagagagaag tgttatatat caaataatgg tggacagatt ttacgataga     120
aacccaacaa ataacgaacc cttctatgat ccagagaaga aaaactacag gctctattgg     180
ggaggagaca ttgaaggcat catagagaga cttgactata tagagagtct aggtgtttca     240
atgatatggc tttcaccatt aaacgacaac ataaacagaa tggcaggtgg aagcgctcct     300
tatcatgggt attggccaag agacttcaaa aggatagacg agcactttgg cacctgggaa     360
gactttagaa ggttagtaga agaagctaag aaaagaggaa tttgcataat agtagactat     420
gtccccaacc attcaaatcc agcaactgat ggggagtttg agctttgta cgataatgga     480
acattagtga ctaactacta tgaagacaga aaaaatgcca caagaaatcc ctatactgcg     540
agcctggaaa acatctatca ccacaatggc aacataaacg attggtttgg ctttcagctt     600
aagtacgcaa atctttttgg attggcagat ttcaaccaaa tgaatgactt tgtggataat     660
tatcttaaag aagggggcagc tttattcgtg aaaaatggcg cttgtggatt tagaattgat     720
gctgttaagc atatagagct gggatggctt gaaaccttct accttttacct atatcaaatc     780
tcagatgaac cactctttat ctacggagaa tactttgcaa acactcctga caaaacgttt     840
gacctctatg agttctatag gtactcaaat gtatcttccc tcttaaatat cccaattaga     900
gaatcaattg cgagaacttt tgcatatgga ggaagttttg agcagctagc aaagatgtta     960
gaggagtatt acagtttgtt cgtttatccc aacaagcagt tgaacttctt agacagccat    1020
gatttagtta ggttcctgaa catgaaccca acaaagaca ggtaccacat ggccctcgga    1080
ttagtaatga cactcccagg aattcctgtt atatattatg gagatgaaag ctatttagtg    1140
agtaaggaag ggaagggaga ccctacaac agaccaatga tggttttga taactctact    1200
aaggctgctg agattataag aaagcttca ttgctaagaa aagtcaacga tgcccttgct    1260
tatagtgatt tcagaaccgt atatgtggac tacaacacat ggatatttga gagaaagttt    1320
ggaagccaca agatattagt tgctctaaac aaagggccag acaaaaacat cacgatttcc    1380
ctaaactgga cagatggaac atacatagac atcatcgaag gagcaattct caaagttaaa    1440
gaaggtcagg gtgagataaa gctacccaga tattcattttt atgtctttca tgtagaggaa    1500
```

-continued

```
gaacagaaaa cccctctcat aggatctata actccataca tagcccaacc tgggcaaaaa    1560
atccttatag ccggagcagg cctcaatgga acatcaagg tgtatatagg aggtaggaga     1620
gcaagaatta ttgagaaaga agaaaattcc atccttgtag aggttcccga gattaaaact    1680
atgaatgcgt ggattcctgt ttgggttgtt gttaatggaa ctagaagcaa tgaggttaag    1740
cttaggtact attctagcaa tgatatccca gcactaatag tcctacaagg aaactacact    1800
ggttaccttt gggtcaaggg gaacatacca gaactctcag agccgagacc cctcttgaaa    1860
tctccaacgg gacactactt tgccgtggtt cccctcccca gaaacaaaac ttttacagtt    1920
caactatata agggacttcc ctgggaacct ctccaaccaa caaatgtcac gttgtatgga    1980
attggaaata aaacagtaat attgaatgaa gccgctccag aaactcctgt atgcggccca    2040
ggaattgtcg cagtatttgc acttctccca ttgttaaaaa gaaaaagaa aaagtcaccc     2100 aacaccacaa taactcccata cggagtaccc atagtagccg ttagctggat cgtgaggtgg   2160
tgcctctag                                                           2169
```

<210> SEQ ID NO 3
<211> LENGTH: 29
<212> TYPE: DNA
<213> ORGANISM: Artificial
<220> FEATURE:
<223> OTHER INFORMATION: PCR primer am1-F1 for amplifying a gene
      encoding a polypeptide having a glucoamylase activity from
      Pyrococcus furiosus.

<400> SEQUENCE: 3

```
aaagcatgca ctaaaggtga taacatgag                                      29
```

<210> SEQ ID NO 4
<211> LENGTH: 29
<212> TYPE: DNA
<213> ORGANISM: Artificial
<220> FEATURE:
<223> OTHER INFORMATION: PCR primer AMY-2N for amplifying a gene
      encoding a polypeptide having a glucoamylase activity from
      Pyrococcus furiosus.

<400> SEQUENCE: 4

```
gcaggtcgac ggatcacgtg aacataaag                                      29
```

<210> SEQ ID NO 5
<211> LENGTH: 3519
<212> TYPE: DNA
<213> ORGANISM: Pyrococcus furiosus

<400> SEQUENCE: 5

```
aaagcatgca ctaaaggtga taacatgaga aagctgataa taagttttac aattcttgta    60
ctctattttt cccaggtcgc aagcctatta tgttccagag agaagtgtta tatatcaaat    120
aatggtggac agattttacg atagaaaccc aacaaataac gaacccttct atgatccaga    180
gaagaaaaac tacaggctct attggggagg agacattgaa ggcatcatag agagacttga    240
ctatatagag agtctaggtg tttcaatgat atggctttca ccattaaacg acaacataaa    300
cagaatggca ggtggaagcg ctccttatca tgggtattgg ccaagagact tcaaaaggat    360
agacgagcac tttggcacct gggaagactt tagaaggtta gtagaagaag ctaagaaaag    420
aggaatttgc ataatagtag actatgtccc caaccattca atccagcaa ctgatgggga    480 gtttggagct ttgtacgata tggaacatt agtgactaac tactatgaag acagaaaaa     540
```

```
tgccacaaga aatccctata ctgcgagcct ggaaaacatc tatcaccaca atggcaacat    600
aaacgattgg tttggctttc agcttaagta cgcaaatctt tttggattgg cagatttcaa    660
ccaaatgaat gactttgtgg ataattatct taaagaaggg gcagctttat tcgtgaaaaa    720
tggcgcttgt ggatttagaa ttgatgctgt taagcatata gagctgggat ggcttgaaac    780
cttctacctt tacctatatc aaatctcaga tgaaccactc tttatctacg gagaatactt    840
tgcaaacact cctgacaaaa cgtttgacct ctatgagttc tataggtact caaatgtatc    900
ttccctctta aatatcccaa ttagagaatc aattgcgaga acttttgcat atggaggaag    960
ttttgagcag ctagcaaaga tgttagagga gtattacagt ttgttcgttt atcccaacaa   1020
gcagttgaac ttcttagaca gccatgattt agttaggttc ctgaacatga acccaaacaa   1080
agacaggtac cacatggccc tcggattagt aatgacactc ccaggaattc ctgttatata   1140
ttatggagat gaaagctatt tagtgagtaa ggaagggaag ggagacccct acaacagacc   1200
aatgatggtt tttgataact ctactaaggc tgctgagatt ataagaaagc tttcattgct   1260
aagaaaagtc aacgatgccc ttgcttatag tgatttcaga accgtatatg tggactacaa   1320
cacatggata tttgagagaa agtttggaag ccacaagata ttagttgctc taaacaaagg   1380
gccagacaaa aacatcacga tttccctaaa ctggacagat ggaacataca tagacatcat   1440
cgaaggagca attctcaaag ttaaagaagg tcagggtgag ataaagctac ccagatattc   1500
attttatgtc tttcatgtag aggaagaaca gaaaacccct ctcataggat ctataactcc   1560
atacatagcc caacctgggc aaaaaatcct tatagccgga gcaggcctca atggaaacat   1620
caaggtgtat ataggaggta ggagagcaag aattattgag aaagaagaaa attccatcct   1680
tgtagaggtt cccgagatta aaactatgaa tgcgtggatt cctgtttggg ttgttgttaa   1740
tggaactaga agcaatgagg ttaagcttag gtactattct agcaatgata tcccagcact   1800
aatagtccta caaggaaact acactggtta cctttgggtc aaggggaaca taccagaact   1860
ctcagagccg agacccctct tgaaatctcc aacgggacac tactttgccg tggttcccct   1920
ccccagaaac aaaacttttta cagttcaact atataaggga cttccctggg aacctctcca   1980
accaacaaat gtcacgttgt atggaattgg aaataaaaca gtaatattga atgaagccgc   2040
tccagaaact cctgtatgcg gcccaggaat tgtcgcagta tttgcacttc tcccattgtt   2100
aaaaagaaaa aagaaaaagt cacccaacac cacaataact ccatacggag tacccatagt   2160
agccgttagc tggatcgtga ggtggtgcct ctaggtatac ccatccgcta ctatctactc   2220
ttttatctac ccatcctcct aggtttccag tgtattcatg aatacaagcc cctgcaaact   2280
ttggaacgta tacccaccta ccaacccagt tagggctcaa gttaatgtaa gttataagcc   2340
caggccttct agaatctcca tttctcacaa atatgagctc atcgttgtcg tagtagacaa   2400
ttgttgtgct tcctcctgcc aaatgatcat ggatccaaat gaggttaatt agcttatcct   2460
tgttcagcca ttcctcaaag tccctgtaga atattactgg ctgtccctca tatgtcaata   2520
tgaacgcata tgctggatac ttgttccata ttatatctgt gtcatgattg caacgaaag    2580 ttactgcctt aaatggatct ctcgaaacta cagtttgtcc gttttgtagg gcatagacta   2640
atgctggaat gttgttattg tcaaatgctt catccatttt atagtagagc gggaagtcaa   2700
agaccttgtc accactctca tatgcccagc ttagtagtgc atctacattt gtgtcccagt   2760
actctccaac tgcccaacct ccccaccaat taagccagtc tctgacaacc caagctccat   2820
agcccttaac atagtcaaat ctccaaccat caaatcctat gcttcttaaa taagcagcat   2880
aactctcatt gctcttccat agccagtact gatcccactc tttgtgatga catatatctg   2940
```

```
gaaatcctcc aaaggttcct tcgtcacaac aatgaagctc gtttggatgg aagtccagat      3000
agttagctgt atatttccct gaggcaactt tagaaaagtc tgtccatgtg taatctccaa      3060 cgaagggtt ccattctagg tcaccaccag ccctgtggtt tataactaca tcggcgatta      3120
cctttattcc ataggcatgg gcagtttgta tcaatctcac tagttcttct tttgatccaa      3180
aacgcgtctc tacagttccc ttctggtagt actcgccgag atcaaagtaa tcatagggat      3240
cgtagcccat tgaatatcct ccactcatcc ccttgcttgg tggaggtagc catattgcag      3300
agattccagc ttcataccat tcaggaatct tcgatcttat atgatcccac caaattcctc      3360
cccctggaac atcccaatag aatgcttgca ttataactcc tccctcttca agctccaagt      3420
attttgctgc acttactgga cttgctagta ctataaaaaa cagtaataga gttaggaggg      3480
gtgttaattt ctttatgttc acgtgatccg tcgacctgc                             3519
```

<210> SEQ ID NO 6
<211> LENGTH: 703
<212> TYPE: PRT
<213> ORGANISM: Pyrococcus furiosus

<400> SEQUENCE: 6

```
Ala Tyr Tyr Val Pro Glu Arg Ser Val Ile Tyr Gln Ile Met Val Asp
1               5                   10                  15

Arg Phe Tyr Asp Arg Asn Pro Thr Asn Asn Glu Pro Phe Tyr Asp Pro
                20                  25                  30

Glu Lys Lys Asn Tyr Arg Leu Tyr Trp Gly Gly Asp Ile Glu Gly Ile
            35                  40                  45

Ile Glu Arg Leu Asp Tyr Ile Glu Ser Leu Gly Val Ser Met Ile Trp
        50                  55                  60

Leu Ser Pro Leu Asn Asp Asn Ile Asn Arg Met Ala Gly Gly Ser Ala
65                  70                  75                  80

Pro Tyr His Gly Tyr Trp Pro Arg Asp Phe Lys Arg Ile Asp Glu His
                85                  90                  95

Phe Gly Thr Trp Glu Asp Phe Arg Arg Leu Val Glu Glu Ala Lys Lys
            100                 105                 110

Arg Gly Ile Cys Ile Ile Val Asp Tyr Val Pro Asn His Ser Asn Pro
        115                 120                 125

Ala Thr Asp Gly Glu Phe Gly Ala Leu Tyr Asp Asn Gly Thr Leu Val
    130                 135                 140

Thr Asn Tyr Tyr Glu Asp Arg Lys Asn Ala Thr Arg Asn Pro Tyr Thr
145                 150                 155                 160

Ala Ser Leu Glu Asn Ile Tyr His His Asn Gly Asn Ile Asn Asp Trp
                165                 170                 175

Phe Gly Phe Gln Leu Lys Tyr Ala Asn Leu Phe Gly Leu Ala Asp Phe
            180                 185                 190

Asn Gln Met Asn Asp Phe Val Asp Asn Tyr Leu Lys Glu Gly Ala Ala
        195                 200                 205

Leu Phe Val Lys Asn Gly Ala Cys Gly Phe Arg Ile Asp Ala Val Lys
    210                 215                 220

His Ile Glu Leu Gly Trp Leu Glu Thr Phe Tyr Leu Tyr Leu Tyr Gln
225                 230                 235                 240

Ile Ser Asp Glu Pro Leu Phe Ile Tyr Gly Glu Tyr Phe Ala Asn Thr
                245                 250                 255

Pro Asp Lys Thr Phe Asp Leu Tyr Glu Phe Tyr Arg Tyr Ser Asn Val
            260                 265                 270
```

-continued

```
Ser Ser Leu Leu Asn Ile Pro Ile Arg Glu Ser Ile Ala Arg Thr Phe
        275                 280                 285

Ala Tyr Gly Gly Ser Phe Glu Gln Leu Ala Lys Met Leu Glu Glu Tyr
    290                 295                 300

Tyr Ser Leu Phe Val Tyr Pro Asn Lys Gln Leu Asn Phe Leu Asp Ser
305                 310                 315                 320

His Asp Leu Val Arg Phe Leu Asn Met Asn Pro Asn Lys Asp Arg Tyr
                325                 330                 335

His Met Ala Leu Gly Leu Val Met Thr Leu Pro Gly Ile Pro Val Ile
            340                 345                 350

Tyr Tyr Gly Asp Glu Ser Tyr Leu Val Ser Lys Glu Gly Lys Gly Asp
        355                 360                 365

Pro Tyr Asn Arg Pro Met Met Val Phe Asp Asn Ser Thr Lys Ala Ala
    370                 375                 380

Glu Ile Ile Arg Lys Leu Ser Leu Leu Arg Lys Val Asn Asp Ala Leu
385                 390                 395                 400

Ala Tyr Ser Asp Phe Arg Thr Val Tyr Val Asp Tyr Asn Thr Trp Ile
                405                 410                 415

Phe Glu Arg Lys Phe Gly Ser His Lys Ile Leu Val Ala Leu Asn Lys
            420                 425                 430

Gly Pro Asp Lys Asn Ile Thr Ile Ser Leu Asn Trp Thr Asp Gly Thr
        435                 440                 445

Tyr Ile Asp Ile Ile Glu Gly Ala Ile Leu Lys Val Lys Glu Gly Gln
    450                 455                 460

Gly Glu Ile Lys Leu Pro Arg Tyr Ser Phe Tyr Val Phe His Val Glu
465                 470                 475                 480

Glu Glu Gln Lys Thr Pro Leu Ile Gly Ser Ile Thr Pro Tyr Ile Ala
                485                 490                 495

Gln Pro Gly Gln Lys Ile Leu Ile Ala Gly Ala Gly Leu Asn Gly Asn
            500                 505                 510

Ile Lys Val Tyr Ile Gly Gly Arg Arg Ala Arg Ile Ile Glu Lys Glu
        515                 520                 525

Glu Asn Ser Ile Leu Val Glu Val Pro Glu Ile Lys Thr Met Asn Ala
    530                 535                 540

Trp Ile Pro Val Trp Val Val Asn Gly Thr Arg Ser Asn Glu Val
545                 550                 555                 560

Lys Leu Arg Tyr Tyr Ser Ser Asn Asp Ile Pro Ala Leu Ile Val Leu
                565                 570                 575

Gln Gly Asn Tyr Thr Gly Tyr Leu Trp Val Lys Gly Asn Ile Pro Glu
            580                 585                 590

Leu Ser Glu Pro Arg Pro Leu Leu Lys Ser Pro Thr Gly His Tyr Phe
        595                 600                 605

Ala Val Val Pro Leu Pro Arg Asn Lys Thr Phe Thr Val Gln Leu Tyr
    610                 615                 620

Lys Gly Leu Pro Trp Glu Pro Leu Gln Pro Thr Asn Val Thr Leu Tyr
625                 630                 635                 640

Gly Ile Gly Asn Lys Thr Val Ile Leu Asn Glu Ala Ala Pro Glu Thr
                645                 650                 655

Pro Val Cys Gly Pro Gly Ile Val Ala Val Phe Ala Leu Leu Pro Leu
            660                 665                 670

Leu Lys Arg Lys Lys Lys Lys Ser Pro Asn Thr Thr Ile Thr Pro Tyr
        675                 680                 685
```

Gly Val Pro Ile Val Ala Val Ser Trp Ile Val Arg Trp Cys Leu
    690              695              700

<210> SEQ ID NO 7
<211> LENGTH: 2112
<212> TYPE: DNA
<213> ORGANISM: Pyrococcus furiosus

<400> SEQUENCE: 7

| | | | | |
|---|---|---|---|---|
| gcctattatg | ttccagagag | aagtgttata | tatcaaataa | tggtggacag | attttacgat | 60 |
| agaaacccaa | caaataacga | acccttctat | gatccagaga | agaaaaacta | caggctctat | 120 |
| tggggaggag | acattgaagg | catcatagag | agacttgact | atatagagag | tctaggtgtt | 180 |
| tcaatgatat | ggcttttcacc | attaaacgac | aacataaaca | gaatggcagg | tggaagcgct | 240 |
| ccttatcatg | ggtattggcc | aagagacttc | aaaaggatag | acgagcactt | tggcacctgg | 300 |
| gaagactttta | gaaggttagt | agaagaagct | aagaaaagag | gaatttgcat | aatagtagac | 360 |
| tatgtcccca | accattcaaa | tccagcaact | gatggggagt | ttggagcttt | gtacgataat | 420 |
| ggaacattag | tgactaacta | ctatgaagac | agaaaaaatg | ccacaagaaa | tccctatact | 480 |
| gcgagcctgg | aaaacatcta | tcaccacaat | ggcaacataa | acgattggtt | tggctttcag | 540 |
| cttaagtacg | caaatctttt | tggattggca | gatttcaacc | aaatgaatga | ctttgtggat | 600 |
| aattatctta | agaaggggc | agctttattc | gtgaaaaatg | gcgcttgtgg | atttagaatt | 660 |
| gatgctgtta | agcatataga | gctgggatgg | cttgaaacct | tctacccttta | cctatatcaa | 720 |
| atctcagatg | aaccactctt | tatctacgga | gaatactttg | caaacactcc | tgacaaaacg | 780 |
| tttgacctct | atgagttcta | taggtactca | aatgtatctt | ccctcttaaa | tatcccaatt | 840 |
| agagaatcaa | ttgcgagaac | ttttgcatat | ggaggaagtt | ttgagcagct | agcaaagatg | 900 |
| ttagaggagt | attacagttt | gttcgtttat | cccaacaagc | agttgaactt | cttagacagc | 960 |
| catgatttag | ttaggttcct | gaacatgaac | ccaaacaaag | acaggtacca | catggccctc | 1020 |
| ggattagtaa | tgacactccc | aggaattcct | gttatatatt | atggagatga | aagctatttta | 1080 |
| gtgagtaagg | aagggaaggg | agaccccctac | aacagaccaa | tgatggtttt | tgataactct | 1140 |
| actaaggctg | ctgagattat | aagaaagctt | tcattgctaa | gaaaagtcaa | cgatgccctt | 1200 |
| gcttatagtg | atttcagaac | cgtatatgtg | gactacaaca | catggatatt | tgagagaaag | 1260 |
| tttggaagcc | acaagatatt | agttgctcta | acaaagggc | cagacaaaaa | catcacgatt | 1320 |
| tccctaaact | ggacagatgg | aacatacata | gacatcatcg | aaggagcaat | tctcaaagtt | 1380 |
| aaagaaggtc | aggtgagat | aaagctaccc | agatattcat | tttatgtctt | tcatgtagag | 1440 |
| gaagaacaga | aaaccctct | cataggatct | ataactccat | acatagccca | acctgggcaa | 1500 |
| aaaatcctta | tagccggagc | aggcctcaat | ggaaacatca | aggtgtatat | aggaggtagg | 1560 |
| agagcaagaa | ttattgagaa | agaagaaaat | tccatccttg | tagaggttcc | cgagattaaa | 1620 |
| actatgaatg | cgtggattcc | tgtttgggtt | gttgttaatg | aactagaag | caatgaggtt | 1680 |
| aagcttaggt | actattctag | caatgatatc | ccagcactaa | tagtcctaca | aggaaactac | 1740 |
| actggttacc | tttgggtcaa | ggggaacata | ccagaactct | cagagccgag | acccctcttg | 1800 |
| aaatctccaa | cgggacacta | cttttgccgtg | gttcccctcc | ccagaaacaa | aacttttaca | 1860 |
| gttcaactat | ataagggact | tccctgggaa | cctctccaac | caacaaatgt | cacgttgtat | 1920 |
| ggaattggaa | ataaaacagt | aatattgaat | gaagccgctc | cagaaactcc | tgtatgcggc | 1980 |
| ccaggaattg | tcgcagtatt | tgcacttctc | ccattgttaa | aagaaaaaa | gaaaagtca | 2040 |

```
cccaacacca caataactcc atacggagta cccatagtag ccgttagctg gatcgtgagg    2100
tggtgcctct ag                                                        2112
```

```
<210> SEQ ID NO 8
<211> LENGTH: 29
<212> TYPE: DNA
<213> ORGANISM: Artificial
<220> FEATURE:
<223> OTHER INFORMATION: PCR primer PX253-01.

<400> SEQUENCE: 8
cgcgccatgg cctattatgt tccagagag                                      29

<210> SEQ ID NO 9
<211> LENGTH: 19
<212> TYPE: DNA
<213> ORGANISM: Artificial
<220> FEATURE:
<223> OTHER INFORMATION: PCR primer R4.

<400> SEQUENCE: 9
tatccatgtg ttgtagtcc                                                 19

<210> SEQ ID NO 10
<211> LENGTH: 32
<212> TYPE: DNA
<213> ORGANISM: Artificial
<220> FEATURE:
<223> OTHER INFORMATION: PCR primer 206S-F.

<400> SEQUENCE: 10
acgcaaatct tagtggattg gcagatttca ac                                  32

<210> SEQ ID NO 11
<211> LENGTH: 32
<212> TYPE: DNA
<213> ORGANISM: Artificial
<220> FEATURE:
<223> OTHER INFORMATION: PCR primer F206S-R.

<400> SEQUENCE: 11
gccaatccac taagatttgc gtacttaagc tg                                  32

<210> SEQ ID NO 12
<211> LENGTH: 30
<212> TYPE: DNA
<213> ORGANISM: Artificial
<220> FEATURE:
<223> OTHER INFORMATION: PCR primer P142I-F.

<400> SEQUENCE: 12
agactatgtc attaaccatt caaatccagc                                     30

<210> SEQ ID NO 13
<211> LENGTH: 32
<212> TYPE: DNA
<213> ORGANISM: Artificial
<220> FEATURE:
<223> OTHER INFORMATION: PCR primer P142I-R.

<400> SEQUENCE: 13
tgaatggtta atgacatagt ctactattat gc                                  32

<210> SEQ ID NO 14
<211> LENGTH: 31
```

```
<212> TYPE: DNA
<213> ORGANISM: Artificial
<220> FEATURE:
<223> OTHER INFORMATION: PCR primer L337V-F.

<400> SEQUENCE: 14
tgaacttcgt cgacagccat gatttagtta g                           31

<210> SEQ ID NO 15
<211> LENGTH: 32
<212> TYPE: DNA
<213> ORGANISM: Artificial
<220> FEATURE:
<223> OTHER INFORMATION: PCR primer L337V-R.

<400> SEQUENCE: 15
catggctgtc gacgaagttc aactgcttgt tg                          32

<210> SEQ ID NO 16
<211> LENGTH: 19
<212> TYPE: DNA
<213> ORGANISM: Artificial
<220> FEATURE:
<223> OTHER INFORMATION: PCR primer F2.

<400> SEQUENCE: 16
ctttagaagg ttagtagaa                                         19

<210> SEQ ID NO 17
<211> LENGTH: 20
<212> TYPE: DNA
<213> ORGANISM: Artificial
<220> FEATURE:
<223> OTHER INFORMATION: PCR primer F3.

<400> SEQUENCE: 17
atcttaaaga agggcagct                                         20

<210> SEQ ID NO 18
<211> LENGTH: 20
<212> TYPE: DNA
<213> ORGANISM: Artificial
<220> FEATURE:
<223> OTHER INFORMATION: PCR primerAN2-R1F2.

<400> SEQUENCE: 18
ggggaggaga cattgaaggc                                        20

<210> SEQ ID NO 19
<211> LENGTH: 21
<212> TYPE: DNA
<213> ORGANISM: Artificial
<220> FEATURE:
<223> OTHER INFORMATION: PCR primer R5.

<400> SEQUENCE: 19
aagttcaact gcttgttggg a                                      21

<210> SEQ ID NO 20
<211> LENGTH: 20
<212> TYPE: DNA
<213> ORGANISM: Artificial
```

```
<220> FEATURE:
<223> OTHER INFORMATION: PCR primer R6.

<400> SEQUENCE: 20
acaagcgcca tttttcacga                                              20
```